United States Patent [19]

Lam

[11] Patent Number: 5,030,911
[45] Date of Patent: Jul. 9, 1991

[54] METHOD AND APPARATUS FOR DISPLAYING DEFECTS IN TUBULAR MEMBERS ON A TWO-DIMENSIONAL MAP IN A VARIETY OF DISPLAY MODES

[75] Inventor: Clive C. Lam, Tomball, Tex.

[73] Assignee: Baker Hughes Incorporated, Houston, Tex.

[21] Appl. No.: 424,136

[22] Filed: Oct. 19, 1980

[51] Int. Cl.⁵ .................. G01N 27/82; G01D 9/00; G06F 15/20

[52] U.S. Cl. .................. 324/226; 324/220; 324/242; 346/33 P; 346/33 F; 364/507; 364/518

[58] Field of Search .................. 324/219–221, 324/239–243, 262, 226, 227; 73/622, 623, 638, 639; 340/802; 378/59, 60; 346/33 P, 33 F; 364/481, 507, 518–521, 550

[56] References Cited

U.S. PATENT DOCUMENTS

| | | | |
|---|---|---|---|
| 3,202,914 | 8/1965 | Deem et al. | 324/242 |
| 3,238,448 | 3/1966 | Wood et al. | 324/220 |
| 3,290,167 | 12/1966 | Wood et al. | 324/242 X |
| 3,383,946 | 5/1968 | Justman . | |
| 3,385,130 | 9/1968 | Boice . | |
| 3,535,624 | 10/1970 | Wood . | |
| 3,628,029 | 12/1971 | Tompkins . | |
| 3,683,186 | 8/1972 | Tompkins . | |
| 3,683,187 | 8/1972 | Tompkins . | |
| 3,683,188 | 8/1972 | Hugonin . | |
| 3,684,887 | 8/1972 | Hugonin . | |
| 3,835,323 | 9/1974 | Kahil . | |
| 3,855,465 | 12/1974 | Tompkins . | |
| 4,203,069 | 5/1980 | Davis | 324/220 |
| 4,309,958 | 1/1982 | Jennings . | |
| 4,312,320 | 1/1982 | Jennings . | |
| 4,422,459 | 12/1983 | Simson . | |
| 4,492,115 | 1/1985 | Kahil et al. . | |
| 4,495,587 | 1/1985 | Plante et al. | 364/507 |
| 4,555,665 | 11/1985 | Stanley et al. . | |
| 4,578,642 | 3/1986 | Moake et al. . | |
| 4,611,170 | 9/1986 | Stanley et al. . | |
| 4,629,985 | 12/1986 | Papadimitriou et al. . | |
| 4,629,991 | 12/1986 | Wheeler . | |
| 4,636,727 | 1/1987 | Kahil et al. . | |
| 4,644,271 | 2/1987 | Toth et al. . | |
| 4,675,604 | 8/1987 | Moyer et al. | 324/220 |
| 4,698,590 | 10/1987 | Moake et al. . | |
| 4,704,580 | 11/1987 | Moake et al. . | |
| 4,710,712 | 12/1987 | Bradfield et al. . | |
| 4,715,442 | 12/1987 | Kahil et al. . | |
| 4,755,753 | 7/1988 | Chern . | |
| 4,792,756 | 12/1988 | Lam et al. . | |
| 4,839,593 | 6/1989 | Spies | 324/240 |
| 4,855,677 | 8/1989 | Clark, Jr. et al. | 324/262 X |
| 4,872,120 | 10/1989 | Pagano . | |
| 4,876,506 | 10/1989 | Brown et al. | 324/220 |
| 4,909,091 | 3/1990 | Ellmann et al. | 324/220 X |

FOREIGN PATENT DOCUMENTS

3629066A1 3/1987 Fed. Rep. of Germany .

Primary Examiner—Gerard R. Strecker
Attorney, Agent, or Firm—Felsman, Bradley, Gunter & Dillon

[57] ABSTRACT

A method and apparatus for determining the extent of defects in tubular elements for use in an oil or gas well is disclosed. The apparatus includes an electromagnetic or other suitable inspection device, cooperating with longitudinal and circumferential position detectors for determining the position and configuration of all defects within a tubular member. Signal generating means are provided for producing signals corresponding to the configuration, longitudinal position, and circumferential position of the defects located within the wall of the tubular member. The signals are processed, preferably by a computer, so that the presence, nature, and precise location of each defect is determined and visually displayed at a suitable display means. Display means are provided for generating a two-dimensional visual display wherein the circumferential and longitudinal positions of the defects are selectably displayed.

56 Claims, 24 Drawing Sheets

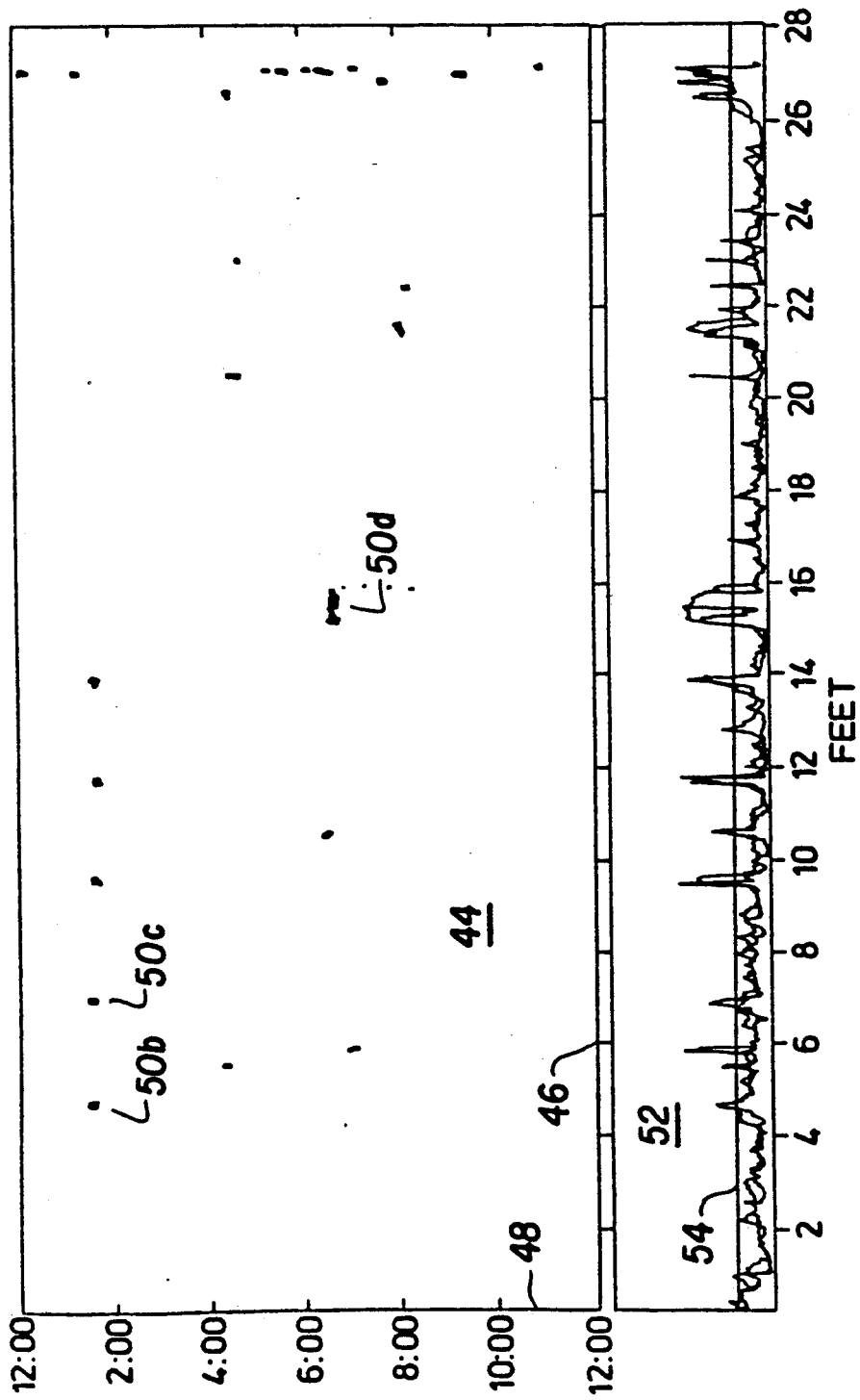

DEFECT SUMMARY

| JOINT NUMBER | LOCATION LONGITUDINAL feet | | TRANSVERSE O clock | ESTIMATION AXIAL length (in) | ORIENT degree |
|---|---|---|---|---|---|
| 1 | 0.31 | ( 0' 3") | 11:48 | 1.3 | multiple |
| 1 | 0.47 | ( 0' 5") | 2:44 | 0.7 | multiple |
| 1 | 1.09 | ( 1' 1") | 9:23 | 0.4 | |
| 1 | 2.49 | ( 2' 5") | 1:28 | 0.4 | |
| 1 | 4.45 | ( 4' 5") | 1:28 | 0.7 | 0 |
| 1 | 5.29 | ( 5' 3") | 4:24 | 0.7 | -11 |
| 1 | 5.62 | ( 5' 7") | 6:56 | 2.0 | 0 |
| 1 | 6.63 | ( 6' 7") | 1:28 | 1.3 | 0 |
| 1 | 7.64 | ( 7' 7") | 4:11 | 0.4 | |
| 1 | 7.75 | ( 7' 8") | 4:20 | 0.4 | |
| 1 | 8.53 | ( 8' 6") | 9:32 | 0.4 | |
| 1 | 9.20 | ( 9' 2") | 1:31 | 3.4 | 0 |
| 1 | 10.21 | ( 10' 2") | 6:31 | 1.3 | 6 |
| 1 | 11.27 | ( 11' 3") | 1:39 | 2.7 | -8 |
| 1 | 12.33 | ( 12' 4") | 6:48 | 0.7 | 0 |
| 1 | 13.34 | ( 13' 4") | 1:36 | 2.7 | multiple |
| 1 | 14.91 | ( 14'10") | 6:39 | 11.4 | 0 |
| 1 | 16.25 | ( 16' 3") | 1:44 | 1.3 | -35 |
| 1 | 17.26 | ( 17' 3") | 1:20 | 2.0 | 33 |
| 1 | 18.32 | ( 18' 3") | 1:23 | 0.7 | 45 |
| 1 | 19.72 | ( 19' 8") | 4:31 | 2.0 | 0 |
| 1 | 20.67 | ( 20' 8") | 8:07 | 4.7 | -6 |
| 1 | 21.17 | ( 21' 2") | 1:31 | 0.4 | |
| 1 | 21.62 | ( 21' 7") | 8:11 | 0.7 | 0 |
| 1 | 22.18 | ( 22' 2") | 4:39 | 2.7 | 3 |
| 1 | 22.57 | ( 22' 6") | 8:07 | 0.7 | 11 |
| 1 | 25.65 | ( 25' 7") | 4:31 | 2.0 | 31 |
| 1 | 26.04 | ( 26' 0") | 9:19 | 4.0 | -50 |

FIG. 5

METHOD AND APPARATUS FOR DISPLAYING DEFECTS IN TUBULAR MEMBERS ON A TWO-DIMENSIONAL MAP IN A VARIETY OF DISPLAY MODES

BACKGROUND OF THE INVENTION

1. Field

This invention relates to defect inspection of tubular elements, and more particularly to displaying the results of such defect inspection in a readily usable format.

2. Description of the Prior Art

Continuous tubular strings formed of connectable tubular sections or elements, such as production tubing strings, drill pipe strings and casing strings, are used in the drilling, completion and production of subterranean oil and gas wells. The individual tubular elements, which are typically steel castings, frequently contain manufacturing defects such as seams, laps, inclusions, and gouges which could result in costly failures if undetected prior to installation. Therefore, tubular elements are commonly inspected at the point of manufacture so that any serious defect can be located and repaired, if possible, before the defective tubing is shipped to the well site.

Tubular elements are also subject to various forms of mechanical damage after being installed within a well. It is therefore advantageous that the individual tubular elements comprising a tubular string be inspected periodically. Typically, the inspection of tubular sections occurs after the individual sections comprising the tubing string have been removed from the well and disengaged. Defect inspections are conventionally performed on a section by section basis.

A number of techniques exist for determining the presence of a defect in a tubing section. For example, the location of internal and external radially extending and three-dimensional defects, including slug inclusions, mechanical damage, pitting and fatigue cracks, has been determined by flux leakage techniques in which a longitudinal magnetic field is induced by one or more magnetic induction coils. External flux detectors are located around the tubing and the maximum signal is recorded to locate the defect. Similarly, longitudinal defects may be detected magnetically by the "rotating pole" method, where the magnetic field is applied from the outside by rotating electromagnets, and flux detectors positioned between the poles scan the outside surface of the pipe. Various techniques relating to electromagnetic inspection are well known in the art with a list of examples being set forth in the following patents:

| | |
|---|---|
| 4,492,115 | 4,636,727 |
| 4,555,665 | 4,698,590 |
| 4,578,642 | 4,704,580 |
| 4,611,170 | 4,710,712 |
| 4,629,985 | 4,715,442 |
| 4,629,991 | 4,792,756 |

While electromagnetic inspection systems have become widely accepted in the industry, various other techniques are also available and may even be preferable depending on the circumstances. Such other inspection techniques include radiation as set forth in U.S. Pat. Nos. 3,835,323 and 3,855,465. Also but less frequently utilized, are ultrasonic inspection systems.

Any of the above mentioned inspection techniques may be utilized to adequately detect the presence of defects located within the wall of tubular elements. The most essential function of existing inspection devices is to generate an electrical signal containing information regarding physical characteristics such as defects and other irregularities in a given segment of a tubular member, and to display such information in a useful manner. Typically, the display consists of a strip chart generated on a strip recorder, indicating the aforementioned electrical signal in analog form with a graphic indication for each irregularity sensed by the detecting device. An inspection crew then utilizes the graph as a guide to visually confirm the existence of serious defects which would result in the rejection of the tubular element being inspected. Conventional graphic displays, however, are severely limited in their ability to convey useful information to the inspection crew responsible for visually locating defects.

A conventional strip chart display provides a very general indication of the existence of a defect and its longitudinal position along the length of a tubular member. The existence of a defect is indicated by one or more vertical peaks in the graph, while the longitudinal position roughly corresponds to the location of the peak (or peaks) along the horizontal axis. If the display contains a plurality of closely adjacent peaks, conventional systems do not distinguish between several closely adjacent defects, a single large defect, or several defects at the same longitudinal position but spaced apart circumferentially. In fact, with respect to the third situation, conventional systems provide virtually no useful information to the inspection crew regarding the circumferential location of any defects. In short, conventional displays provide no usable information regarding the shape, size or amplitude of a defect, and only minimal information regarding the location.

The absence of circumferential position indications in conventional graphic displays becomes an even greater problem when the tubing to be inspected contains a longitudinal weld seam. Since a seam is essentially a continuous irregularity extending from one end of the pipe section to the other, it appears on a conventional graphic display as a continuous string of defects indicated by a solid line of peaks. As such, the weld seam indications on the graphic display completely overshadow all other indications, thus making it virtually impossible to distinguish the weld seam from the defects.

In addition to the imprecise defect locating capabilities of prior art systems, conventional inspection devices typically employ band pass filters to remove extraneous information, such as the presence of certain non-defect irregularities, from the incoming signal. This technique is effective for the intended purpose, but the information filtered out is permanently lost. Conventional systems do not allow the user thereof to include all extreme signal values in the display, if so desired.

SUMMARY OF THE INVENTION

The present invention addresses the deficiencies in prior art inspection systems, including those set forth above. Specifically, the method and apparatus disclosed herein are used to determine the extent of defects occurring in a tubular member, such as a section of tubing used in an oil or gas well, and visually display such defects in a greatly improved manner. A tubing inspection head detects the physical characteristics of a tubular member and generates an electrical signal corresponding thereto. Included in the physical characteristics are defects, and the corresponding electrical signals indicate the presence, angular orientation, and overall configuration of such defects. Additionally, longitudinal and circumferential position detectors generate signals indicating the longitudinal and circumferential position of the inspection head as it moves from one end of the tubular member to the other. A computer receives the signals generated by the inspection head and the longitudinal and circumferential position detectors, correlates the signals to obtain an accurate set of defect data including the size, configuration, orientation, longitudinal position, and circumferential position of every defect within the tubular member. Some or all of the defect data may then be displayed in a two-dimensional format on one or more visual display means.

The computer program utilized to process the signals and display the defect data provides a great deal of flexibility for the present invention. The degree to which the incoming signals are filtered may be selected as desired thus providing for a greater or lesser degree of accuracy as warranted by the situation. The computer program also provides the capability of selectively tailoring the visual display such that various kinds of defects may be emphasized or de-emphasized as desired.

BRIEF DESCRIPTION OF THE DRAWINGS

Other advantages and features of the present invention will become more readily apparent from the following detailed description, when read in conjunction with the accompanying drawings, in which:

FIGS. 4a-4d are examples of the preferred graphical and two-dimensional defect displays produced using principles of the present invention;

FIG. 5 is an example of an alternative defect display in tabular form produced using principles of the present invention.

DESCRIPTION OF THE PREFERRED EMBODIMENT

Figure 1:
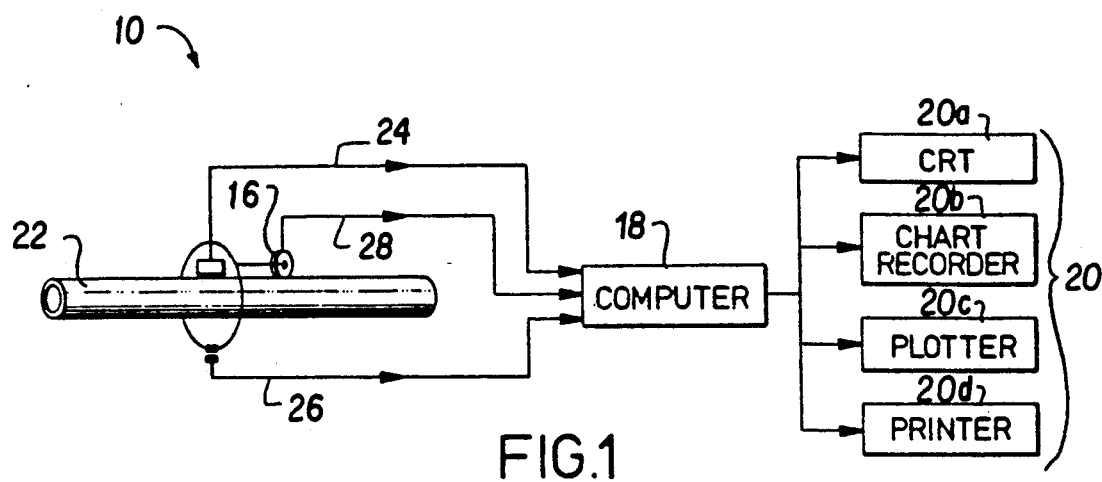
FIG. 1 is a simplified, functional block diagram of the preferred embodiment of the system of the present invention.
Figure 2:
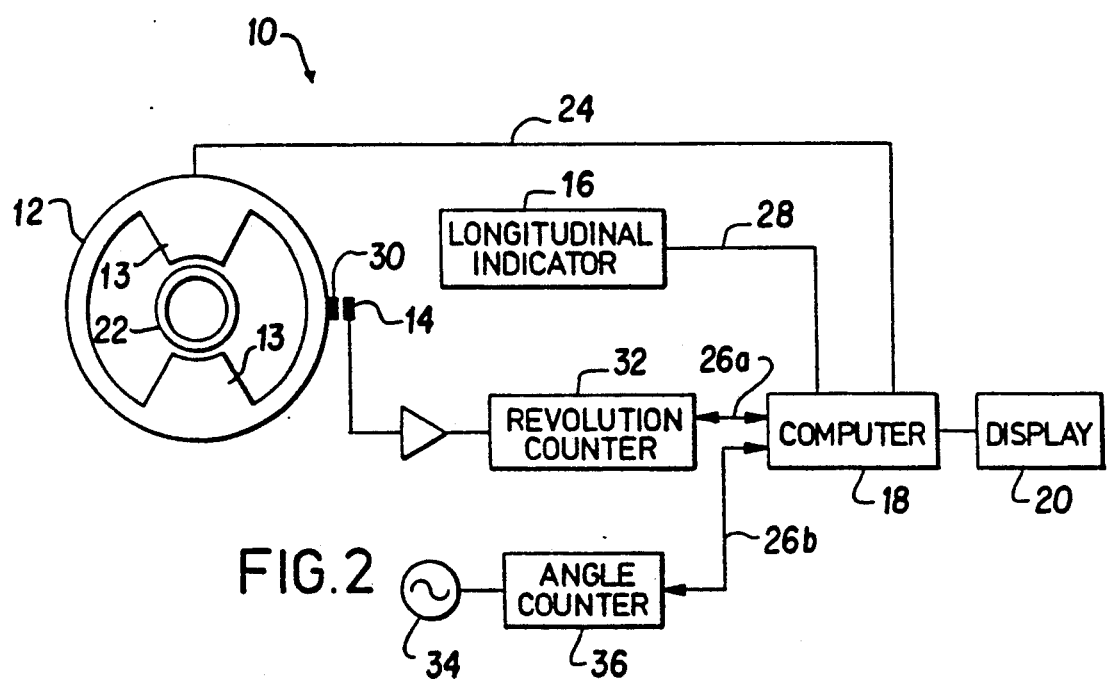
FIG. 2 is a simplified, functional, block diagram of the embodiment of FIG. 1, showing additional features of the preferred circumferential position detector.

FIGS. 1 and 2 provide schematic depictions of the preferred system for carrying out principles of the present invention, with FIG. 2 emphasizing certain features of the preferred apparatus. Referring initially to FIGS. 1 and 2, the principles disclosed herein are preferably embodied in system 10, which generally consists of inspection head 12, circumferential position detector 14, longitudinal position detector 16, a central processing unit or computer 18, and a variety of visual display devices collectively identified by the numeral 20. While it is preferred that system 10 include a CRT 20a, chart recorder 20b, plotter 20c, and printer 20d, it is only necessary for system 10 to include some form of visual display compatible for use with computer 18. It will be understood by those skilled in the art that any number of conventional visual display devices may be suitable for the purposes of the present invention.

As illustrated, system 10 may be effectively employed to accurately determine the extent of defects in a tubular member 22, and visually display the defects in great detail on display device 20. Tubular member 22 typically consists of a single section or joint of pipe associated with oil and gas wells. System 10 may also be incorporated into an on-site inspection facility, wherein an entire tubing string may be conveniently inspected during removal from the well bore. Regardless of whether system 10 is intended for on-site or off-site inspection, the most significant physical requirement is that tubular member 22 and inspection head 12 be movable relative to one another along the longitudinal axis of tubular member 22 to insure complete inspection of tubular member 22 from one end to the other. Typically, off-site inspection, system 10 would include inspection head 12 mounted in a laterally fixed position with tubular member 22 longitudinally movable therethrough by means of a conveyor. For on-site inspection, on the other hand, system 10 would have inspection head 12 vertically fixed above the well bore, and tubular member 22 would be drawn upwardly therethrough during removal from the bore.

During operation of system 10, inspection head 12 comprises the means for generating a defect signal 24, which includes a variety of information about the physical characteristics of tubular member 22. Included in this information are the identification and configuration of any and all defects located within the body of tubular member 22. At any given instant during the operation, inspection head 12 is generating a defect signal 24 representing the characteristics of a single discrete solid segment of tubular member 22. By suitably moving inspection head 12 from one end of tubular member 22 to the other, the content of defect signal 24 is broadened to include information regarding the entire solid volume of tubular member 22, the entire solid volume consisting of the aggregate sum of all discrete solid segments.

As inspection head 12 moves longitudinally relative to tubular member 22, circumferential position detector 14 and longitudinal position detector 16 generate circumferential signal 26 and longitudinal signal 28, respectively, which contain information indicating the location of the defects detected by inspection head 12. Signals 24, 26, and 28 are then directed into computer 18, which utilizes conventional microprocessor circuitry to correlate the signals, thus obtaining a useful set of data concerning the presence, configuration, angular orientation, and precise location of the defects within tubular member 22. This data, referred to herein as "defect data", is then displayed either in its entirety or in selected portions on one or more of the visual display devices 20. Illustrative examples of the visual display provided by the principles of the present invention are set forth in FIGS. 4a-4d and FIG. 5.

Those skilled in the art will recognize that signals 24, 26, and 28 will be generated as analog signals of varying voltages, and must be converted to corresponding digital signals prior to processing by computer 18. It will also be understood that certain filtering networks may be employed in order to effect such conversions. High pass or low pass filters, however, are not necessary to segregate defect data from non-defect data within defect signal 24 due to the unique signal processing features of the present invention, discussed in greater detail below. Of course, defect signal 24 may be segregated by conventional band pass filters without departing from the scope of the present invention. As used herein, defect data relates to those irregularities which would result in the rejection of tubular member 22, while non-defect data relates to less severe irregularities which would not result in such a rejection.

Since defect signal 24 generally contains an enormous volume of information, only a portion of which relates to actual defects, it is necessary to selectively reduce the volume of information so the memory capacity of computer 18 is not exceeded. Rather than applying a conventional low-pass filter to screen out the frequencies normally associated with non-defect irregularities, the present invention includes certain programming steps to enable computer 18 to distinguish defect information from non-defect information. After defect signal 24 has been digitized, the numerical values contained therein are compared by computer 18 to a threshold number selected by the user. The threshold is typically one and one-half times the average numerical value of digitized defect signal 24, but is may be varied as desired depending on the defect tolerances of the user. Computer 18 operates to discard all data having a numerical value less than the threshold, and record the remainder for further processing.

The present invention represents a unique combination of inspection head 12 with circumferential position detector 14 and longitudinal position detector 16, and the principles of this invention are intended to apply regardless of the precise embodiment of these components. In particular, inspection head 12 is preferably intended to be an electromagnetic detection device, such as that disclosed in U.S. Pat. No. 4,710,712, but the teachings of this invention are equally applicable for use with a radiation inspection apparatus, an ultrasonic inspection apparatus, or any other inspection apparatus capable of generating a suitable defect signal 24. For purposes of carrying out the principles of the present invention, the entire specification of U.S. Pat. No. 4,710,712 is hereby incorporated by reference and made a part hereof. The interchangeability of various types of inspection heads will be fully appreciated by those skilled in the art.

The preferred apparatus for carrying out the principles of this invention includes two detector head segments 13, each of which contains twenty-four detecting coils and/or probes for detecting magnetic flux leakage. Therefore, defect signal 24 preferably consists of the multiplexed signals from forty-eight separate flux detectors, each of which is generating a signal, at any given instant, indicative of the defects in a separate discrete solid segment of tubular member 22. It is conceivable, however, that any number of flux detectors could be employed for the purposes disclosed herein. It is understood in the art that a large number of relatively small flux detectors effectively divides tubular member 22 into a greater number of discrete solid segments, thus improving the resolution of the visual display appearing on display device 20.

In the preferred embodiment of the present invention, circumferential position detector 14 is a magnetic sensor which detects each rotation of inspection head 12, by means of magnet 30 which is secured thereto as illustrated in FIG. 2. As such, position detector 14 serves as the sensing means for revolution counter 32, which simply provides computer 18 with a signal 26a indicating the passing of each revolution. To complete the information needed for determining circumferential position, clock 34 and angle counter 36 provide timing signal 26b which is conventionally combined with signal 26a by computer 18 to calculate the rotational position of inspection head 12 at any given instant. Computer 18 then correlates this information with the defect data transmitted by defect signal 24 and the longitudinal position transmitted by longitudinal signal 28 and displays the results on display devices 20 as set forth herein. For convenience and simplicity, revolution counter signal 26a and angle counter signal 26b are cumulatively referred to as circumferential signal 26.

Alternatively, circumferential position detector 14 may consist of any suitable apparatus for determining the circumferential position of the defect detector and generating a corresponding circumferential signal 26. It is expected that with certain "fixed-head" defect detectors, the circumferential position of defects will be indicated by the defect detector itself, and a separate circumferential position detector 14 may be eliminated altogether.

Longitudinal position detector 16 preferably consists of a wheel rotatably secured to a rigid support member such that its outer edge surface bears against the outer surface of tubular member 22. As the wheel of position detector 16 rolls longitudinally along the entire length of tubular member 22, a transducer connected to the wheel generates longitudinal signal 28 which generally corresponds to the distance traveled by the wheel, thus providing computer 18 with sufficient information to determine the longitudinal position of inspection head 12 and any defects detected thereby.

Figure 3:
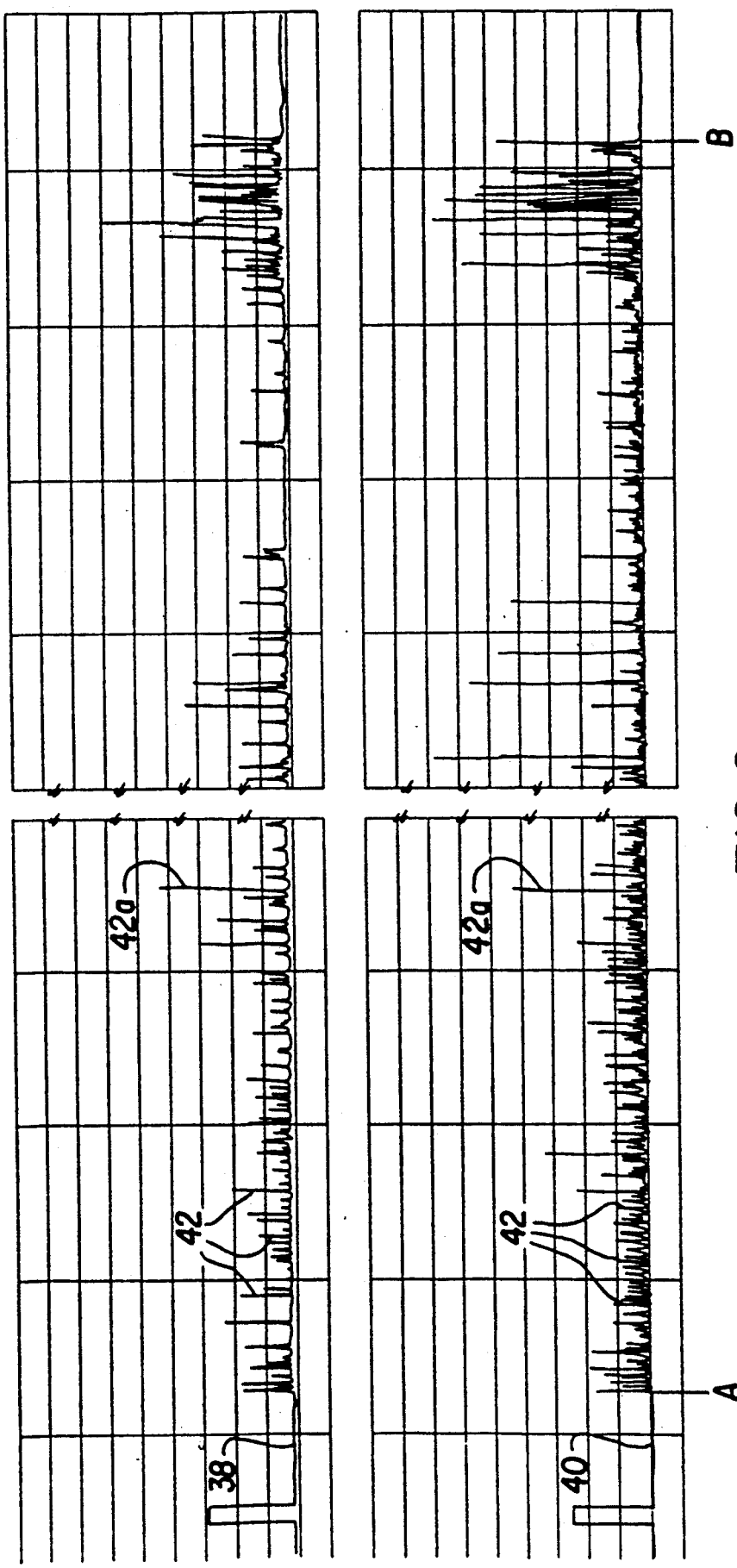
FIG. 3 is a strip chart representative of the defect displaying capability of prior art inspection systems.

To best illustrate the features and advantages of the present invention, it is helpful to start with a typical visual display as provided by the prior art. FIG. 3 is a reproduction of such a display, a strip chart produced on a chart recorder by an electromagnetic inspection system utilizing two detector head segments in a rotating detector apparatus, each head segment generating a separate line on the graphic display. Horizontal axes 38 and 40 each contain a graphic indication of the signal generated by each of the two head segments, with the distance between points A and B corresponding generally to the length of the tubular member inspected. Vertical elements 42 indicate irregularities located within the body of the tubular member, with the longer elements, such as peaks 42a, indicating the most likely presence of a defect. The location of peaks 42a along the horizontal axes 38 and 40 indicate the general longitudinal location of the defects, but the size, configuration, and angular orientation of the defects must be determined by visual inspection. Furthermore, the presence of defects must be visually determined as well, due to the high incidence of false readings and the inability to distinguish between true and false readings. The uncertainty in reading a conventional graphic display is compounded by the overlapping coverage provided by the two detector head segments as they rotate around the pipe.

While most of the tubing presently in use in the oil and gas industry contains no longitudinal seam, there will be occasions from time to time wherein welded tubing containing a longitudinal seam must be inspected. Conventional graphic displays have proven to be inadequate for displaying the results of such inspections, since the presence of the continuous longitudinal seam completely dominates the graphic display to the extent that the display is nothing but a continuous series of peaks which overshadow any indications of defects.

Figure 4A:
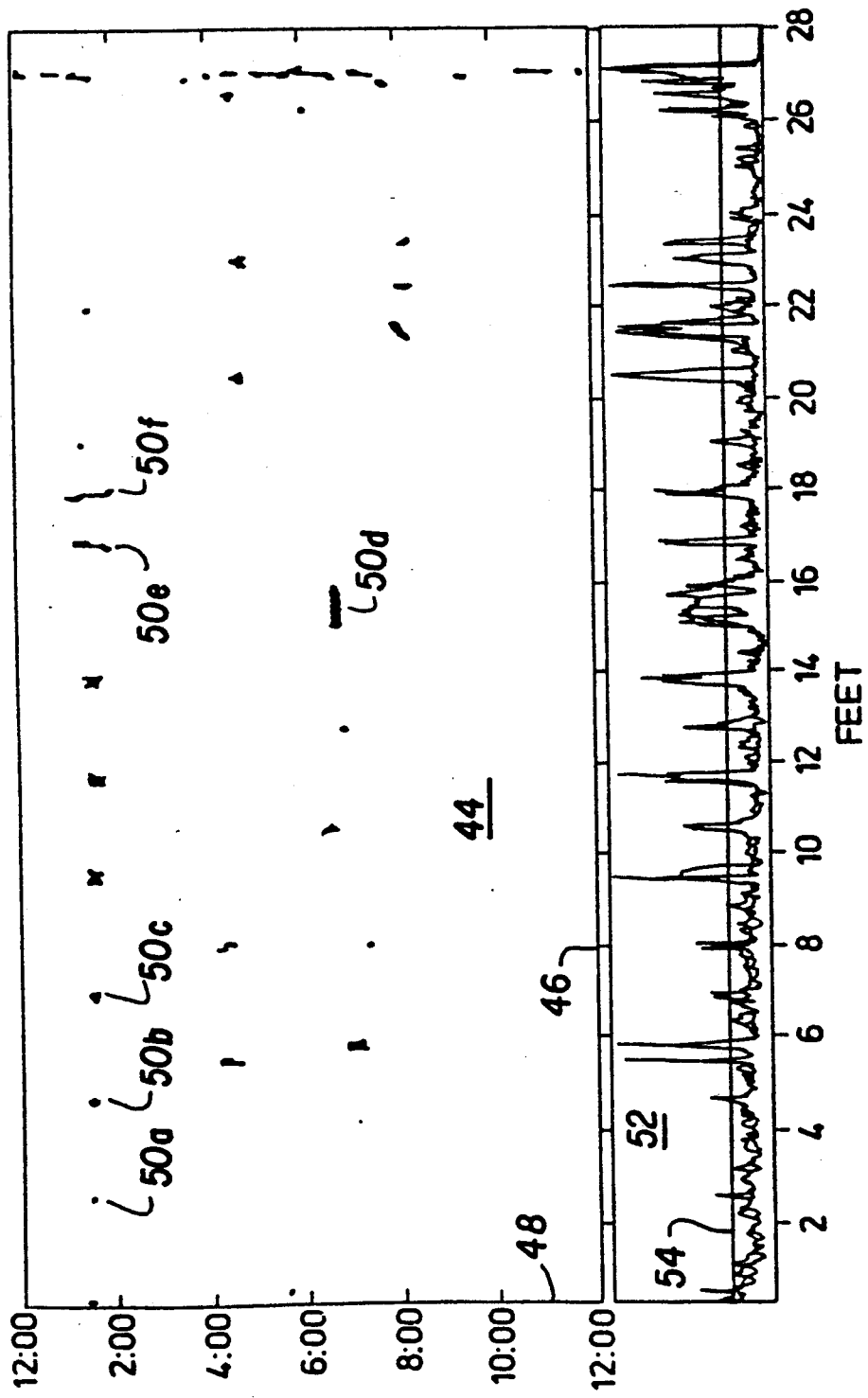

In stark contrast to the crude printout produced by prior art methods and devices, FIGS. 4a–d represent examples of the highly informative graphic displays made possible by the teachings of the present invention. The examples shown may either be observed on a CRT screen, or reproduced on a printer, plotter, or chart recorder. Referring initially to FIG. 4a, it can be seen that the unique function of the present invention yields a two-dimensional map 44 of the defects located within tubular member 22. Preferably, map 44 includes a horizontal axis 46 corresponding generally to the longitudinal length of tubular member 22, and vertical axis 48 corresponding to the circumference of tubular member 22, with the graduation marks along vertical axis 48 signifying degrees of rotation from a pre-selected 12 o'clock position. For purposes of calibrating map 44 with tubular member 22, the twelve o'clock position is noted prior to inspection. Defect identifiers 50a–f indicate the presence, configuration, longitudinal position, and circumferential position of each defect located throughout tubular member 22. When viewed on a CRT screen, defect identifiers 50a–f constitute groups of one or more pixels.

For the sake of convenience and to suit the needs of a particular customer, the defect identifiers may be classified by the relative size of their corresponding defects. Accordingly, defect identifiers 50a, b and c indicate the presence of short defects, 50d indicates the presence of a long defect, and 50e and f indicate the presence of defects having angular orientations, or angle defects. The designations "short", "long", and "angle" are relative terms as used herein, and do not correspond to any particular absolute dimensions of size. The significance of these terms will become apparent in light of the additional features of the preferred embodiment as discussed below.

Positioned immediately beneath map 44 is graph 52, indicating a graphical representation of the signals received from the two head segments 13 of inspection head 12. Rather than indicating the analog signal as with prior art devices, graph 52 depicts the digitized version of defect signal 24 after processing by computer 18. As such, graph 52 is a much more accurate representation of the actual state of defects within tubular member 22.

In the preferred formats shown, the far right-hand side of the display contains certain information regarding the parameters of the procedure and the physical characteristics of the tubing being inspected. In addition to the display mode, this section indicates the threshold value for the display, the rotational velocity (in RPM's) of the inspection head 12, the percentage of coverage provided by the inspection head 12, and the outside diameter, wall thickness, and grade of tubular member 22. Of course, this section of the display may be altered as desired without departing from the principles of this invention.

In order to selectively filter out false or non-defect indications in map 44, graph 52 includes threshold line 54 which may be set or altered according to the particular needs of the customer. The threshold value represented by line 54 serves as a computer generated high pass filter which only allows those values greater than the threshold to appear as defect identifiers on map 44. In the preferred display shown, the threshold value setting is indicated with the information shown to the right of map 44 and graph 52.

Figure 4B:
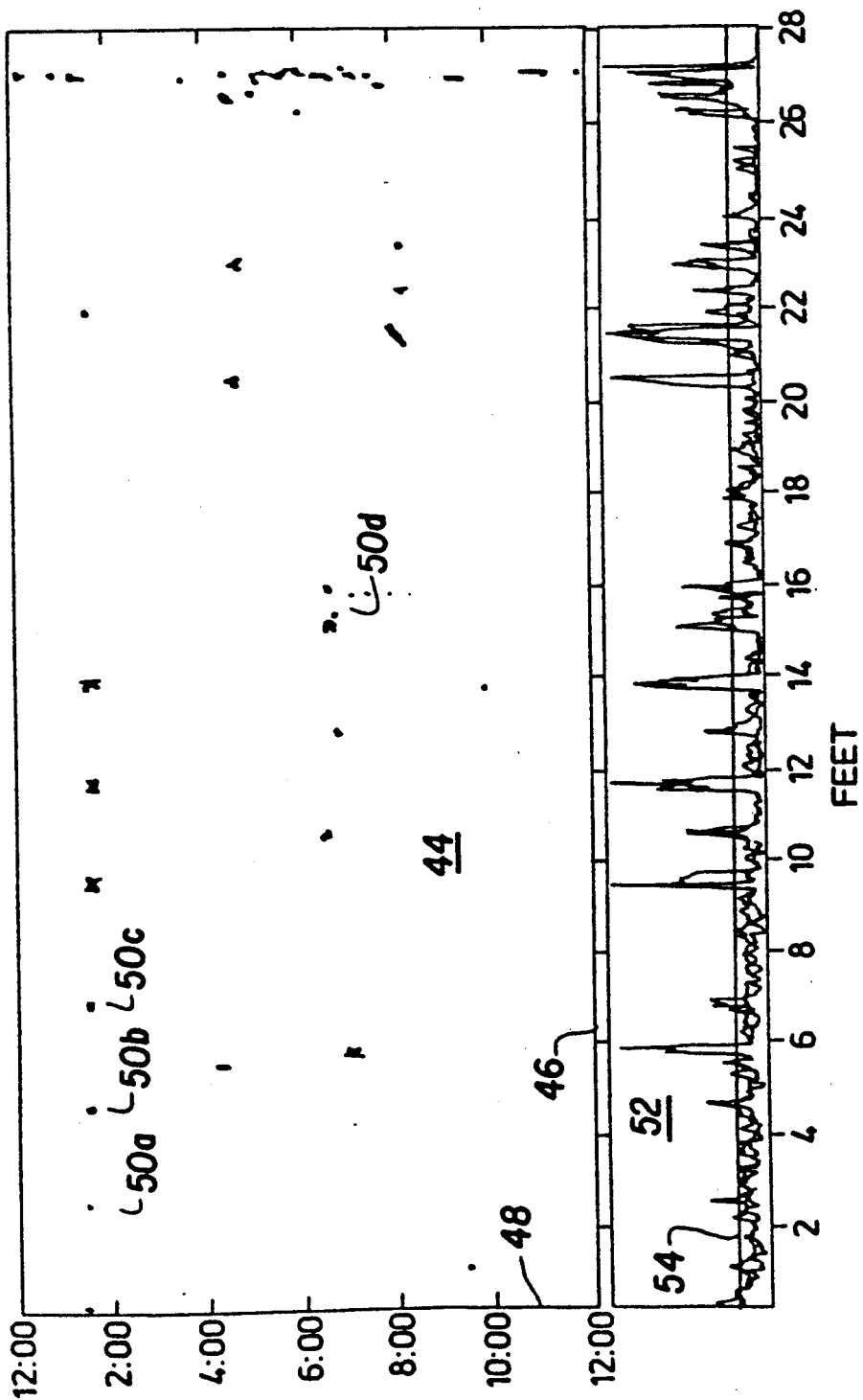
Figure 4C:
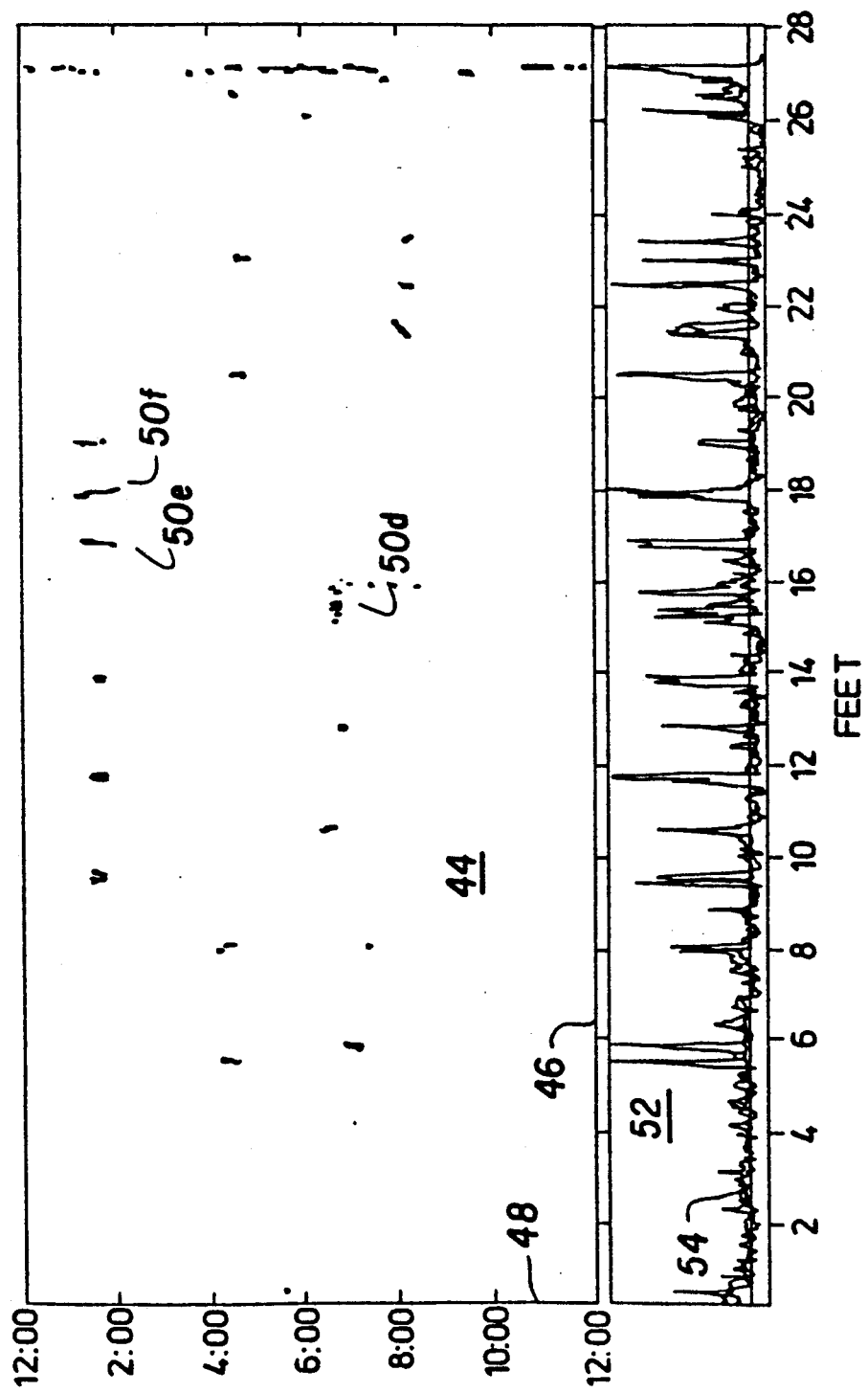

In addition to the threshold value setting, the information shown at the extreme right of FIGS. 4a–d includes the mode selected for the particular display. For the examples shown, FIG. 4a represents a display in the inspection mode, FIG. 4b represents the same display in the set up short mode, FIG. 4c represents the same display in the set up angle mode, and FIG. 4d represents the same display in the set up long mode. Essentially, FIG. 4a is the cumulative version of FIGS. 4b, c, and d, in which short defects, long defects, and angle defects are given substantially equal prominence. In FIG. 4b, on the other hand, the selection of the set up short mode by the user results in additional processing being performed by computer 18 so that short defects are emphasized, with long and angle defects being omitted or shown in a distorted fashion. For example, in FIG. 4b short defect identifiers 50a, b, and c, appear more clearly than in FIG. 4a, whereas long defect identifier 50d appears in broken form and angle identifiers 50e and f do not appear at all. Similarly, in FIG. 4c angle defect identifiers 50e and f are clearly displayed, but short defect identifiers 50a, b, and c have disappeared and long defect identifier 50d appears broken. Finally, FIG. 4d reveals how long defect identifier 50d is emphasized while short defect identifier 50a and angle defect identifiers 50e and f are not shown. The programming steps necessary to isolate the different types of defects and produce the different displays shown in FIGS. 4a–d provide a higher degree of defect identification than is presently known in the industry.

With the preferred embodiment of this invention, it is also possible to display the defect data in tabular form as shown in FIG. 5. The table of FIG. 5 includes four columns of information reflecting the physical characteristics of the defects in tubular member 22. The characteristic shown for each defect are the longitudinal position, the circumferential position, longitudinal or axial length, and the angular orientation.

In FIG. 5, data pertaining to the location of a defect is grouped under the heading "LOCATION," and data pertaining to the length and angular orientation of a defect is grouped under the heading "ESTIMATION." In the table of FIG. 5, information relating to location includes the longitudinal and circumferential (alternately identified in the figure as "traverse") position of the defects. The presentation of defect data in this manner provides a convenient tool for assisting the inspection crew in visually locating each defect. In addition to the four columns of defect data, the preferred table also includes a fifth column headed "joint number" for identifying the section or joint of tubing being A sixth column may be provided (but is not depicted in FIG. 5) headed "Comment" in which the inspection crew may record notes as desired."

To illustrate the convenience of the tabular display set forth in FIG. 5, the appropriate line of data corresponding to long defect identifier 50d has been highlighted and designated by the numeral 55. Upon reading the defect data set forth in line 55, the inspection crew knows that a defect approximately 11.4 inches long may be found, starting at a point 14.91 ft. (or 14 ft. 10 in.) from the leading edge of pipe joint No. 1, located at circumferential position 6:39 and extending essentially parallel to the longitudinal axis of the tubular member. Armed with this knowledge, the inspection crew can relatively easily locate the defect corresponding to identifier 50d, and determine whether the affected section of tubing should be repaired or replaced.

As noted above, the table illustrated in FIG. 5 includes a column specifying the angular orientation of each defect identified. The angular orientation is calculated by computer 18 based upon information contained in defect signal 24, in combination with other known data. As inspection head 12 rotates around tubular member 22 at a constant rotational velocity, defect signal 24 indicates the presence of a plurality of discrete points which, when viewed in their entirety, indicate the presence of an angle defect such as those indicated at 50e and f shown in FIGS. 4a and c. Since an angle defect is, by definition, positioned at an angle with respect to the longitudinal axis of tubular element 22, the detection of two adjacent discrete points on a given angle defect will require slightly more, or slightly less, than one complete revolution of inspection head 12. This phenomenon results in a time differential, or time lag, between the detection of adjacent points on an angle defect and the period of rotation of inspection head 12. Computer 18, being pre-programmed with the rotational and longitudinal velocity of inspection head 12, can then apply conventional mathematical principles to determine the angular displacement of a first point from a second point on an angle defect, the angular displacement typically being determined with reference to the longitudinal axis of tubular member 22. The angular displacement between two discrete points on the defect is thus displayed in FIG. 5 as the angular orientation of the defect.

FIG. 6a through FIG. 12 illustrate a flowchart for the computer program developed to perform the various signal processing functions incorporated into the preferred embodiment of the present invention. While the illustrated flowchart describes the preferred software for carrying out the principles of this invention, it will be understood by those skilled in the art that substantial changes may be made in the computer program without departing from the scope of the invention.

Figure 6A:
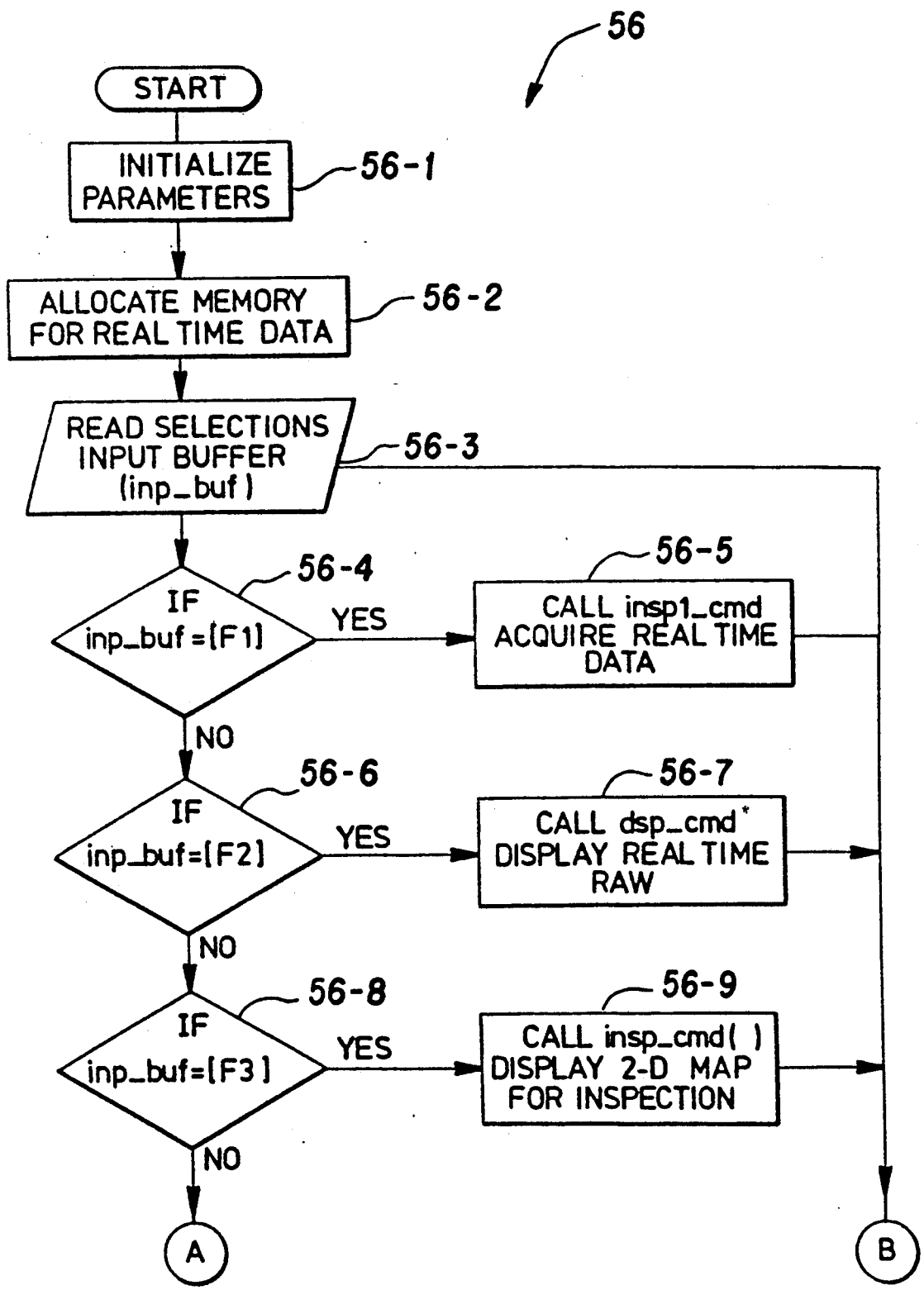
FIGS. 6a-12 are a simplified flowchart of the main computer program and key subroutines which perform the signal processing functions for the preferred embodiment of the present invention.
Figure 6B:
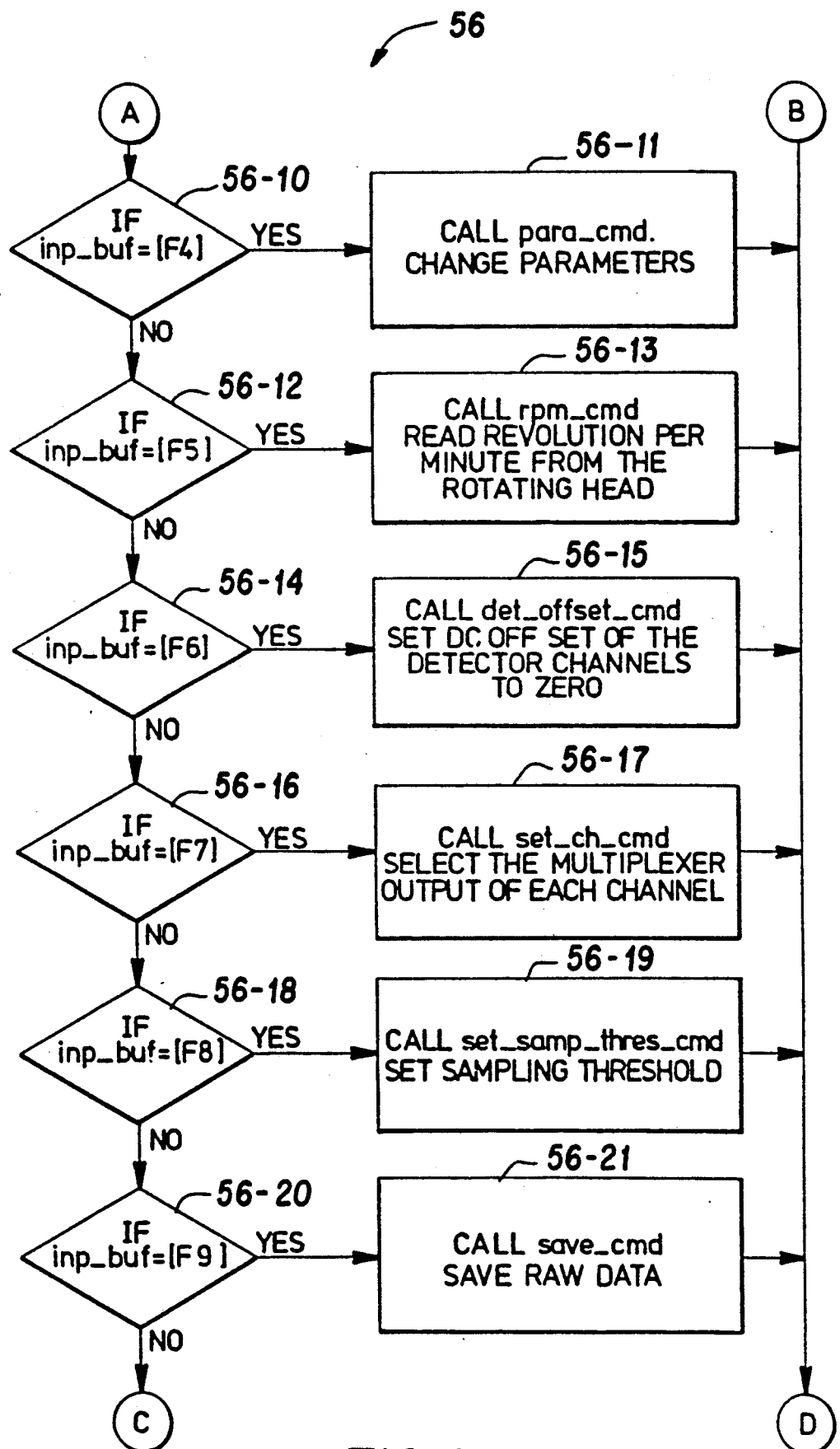
Figure 6C:
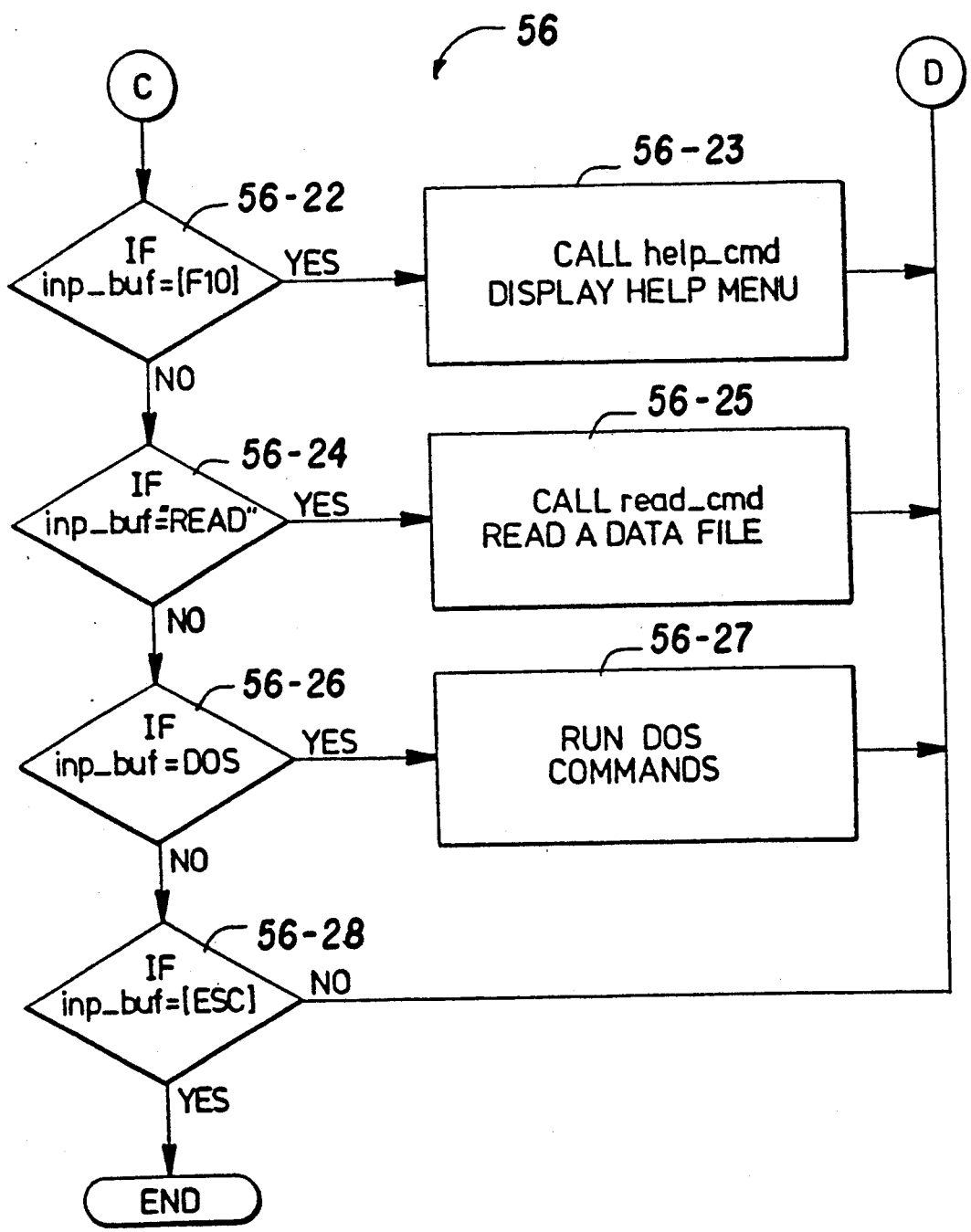
Figure 7A:
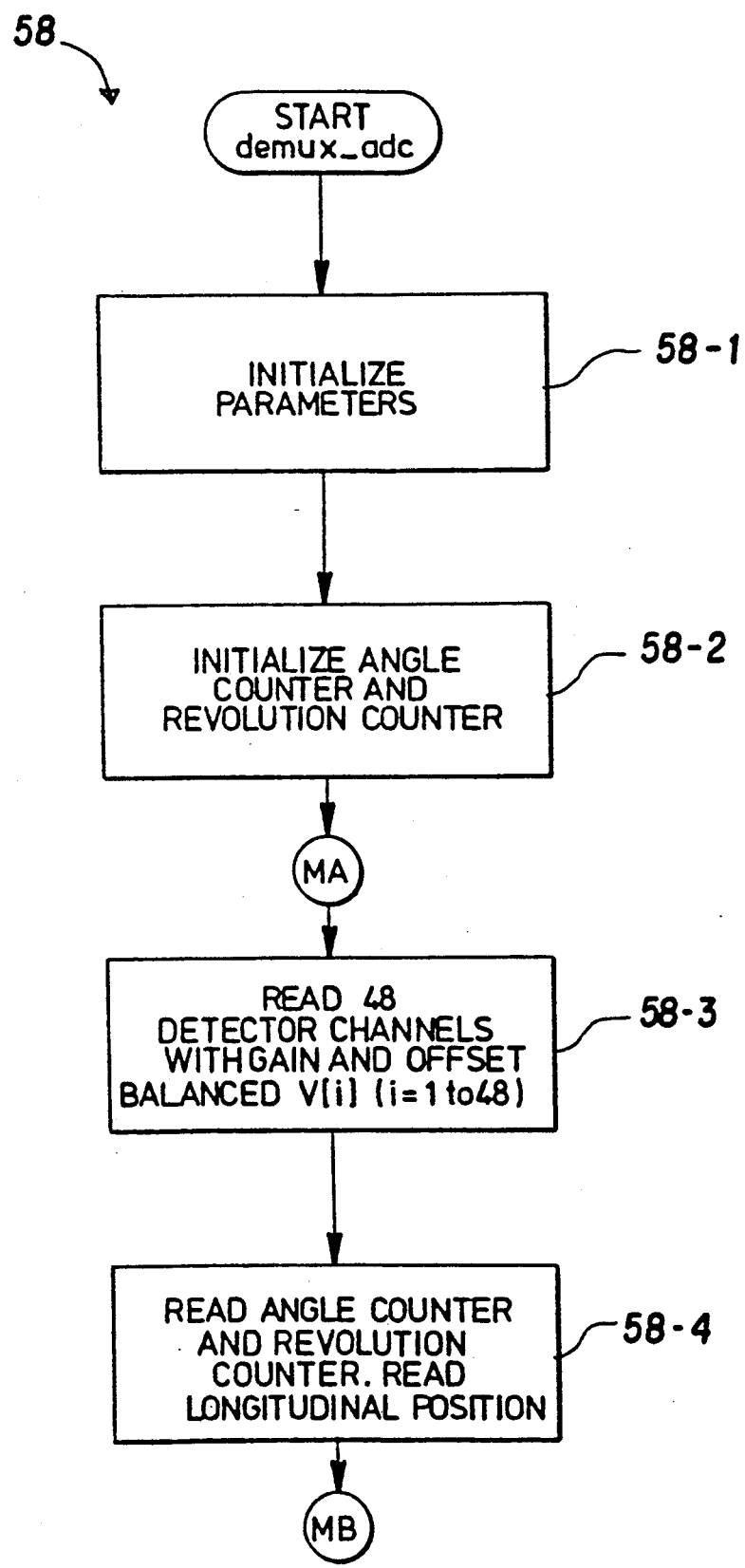
Figure 7B:
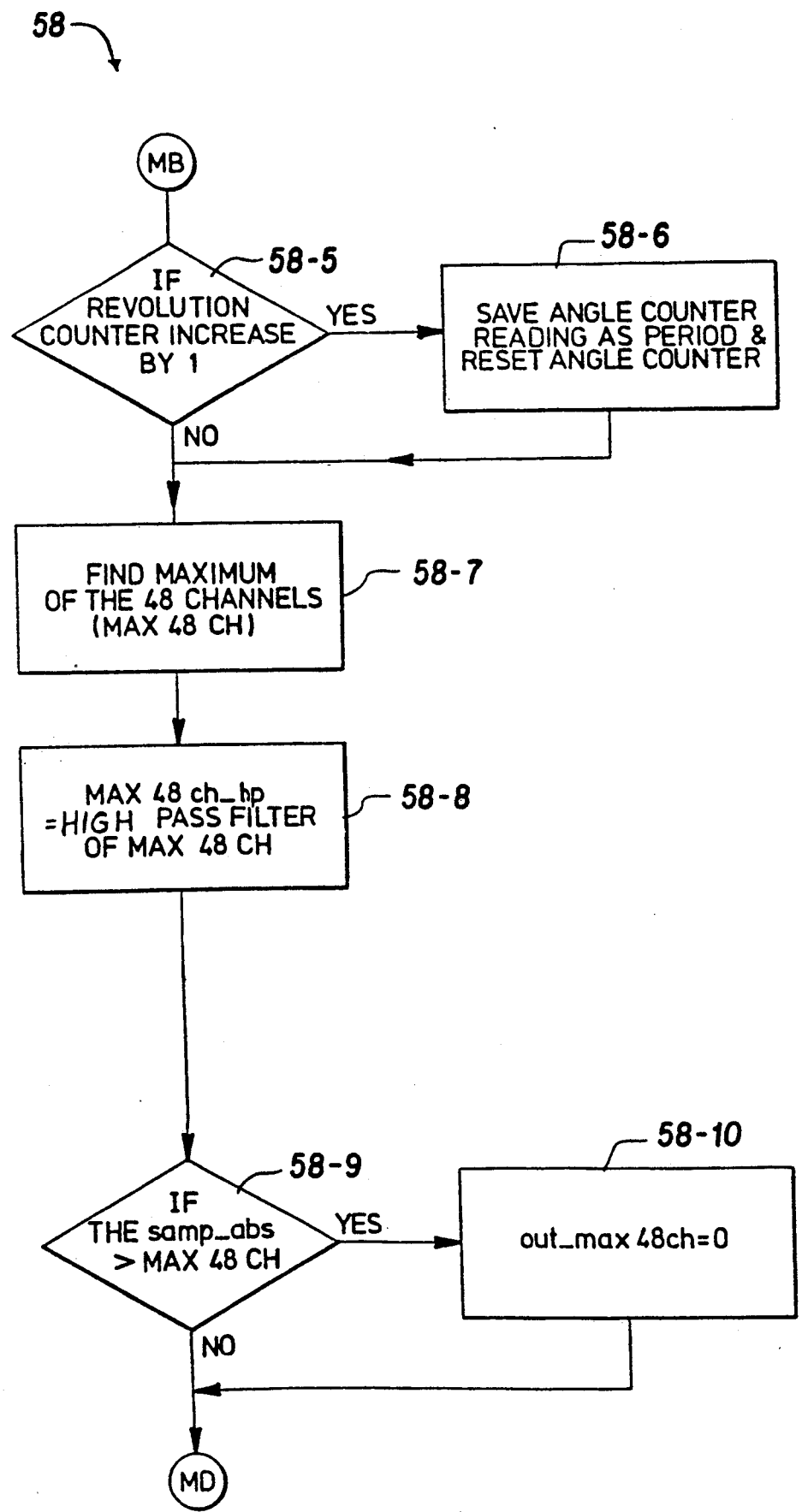
Figure 7C:
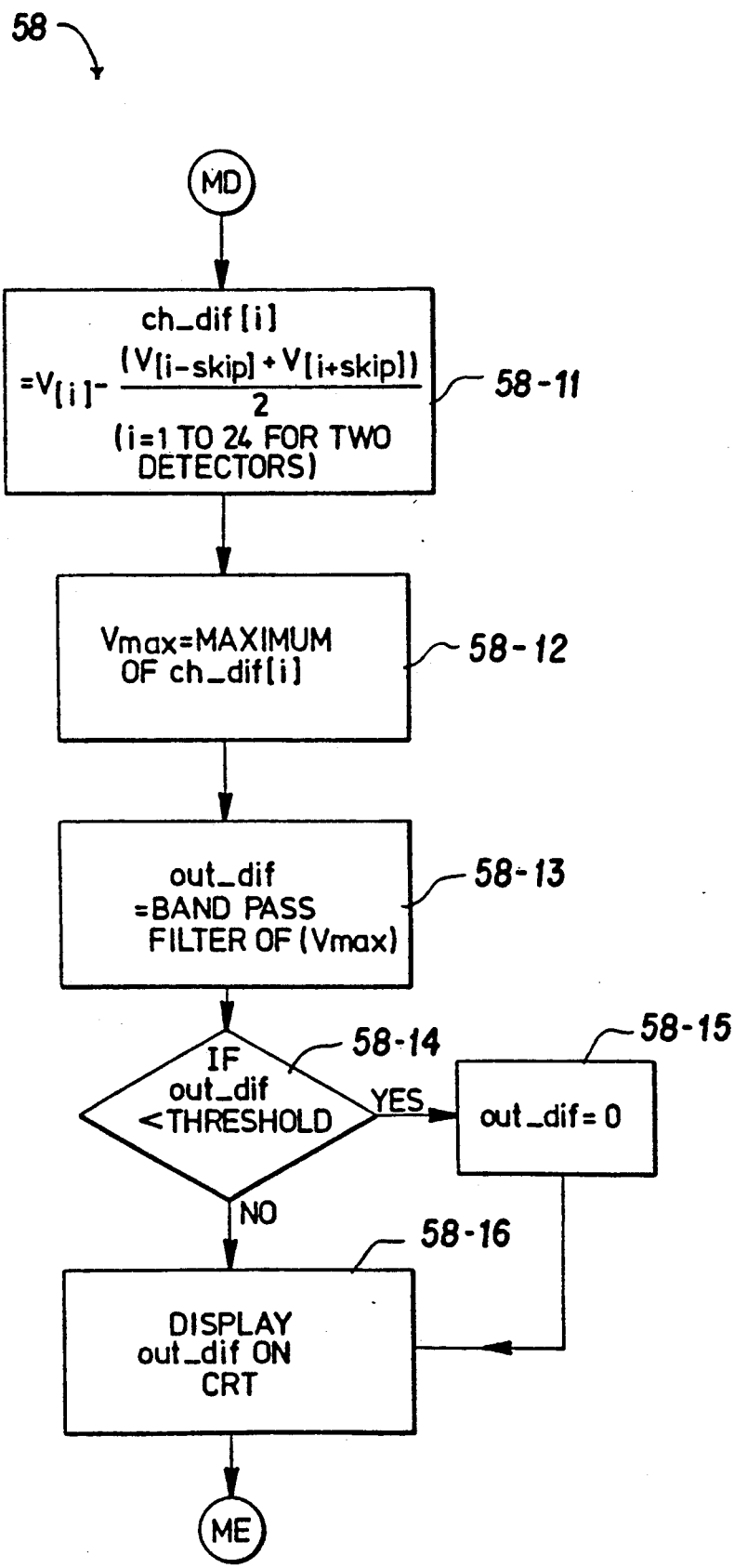
Figure 7D:
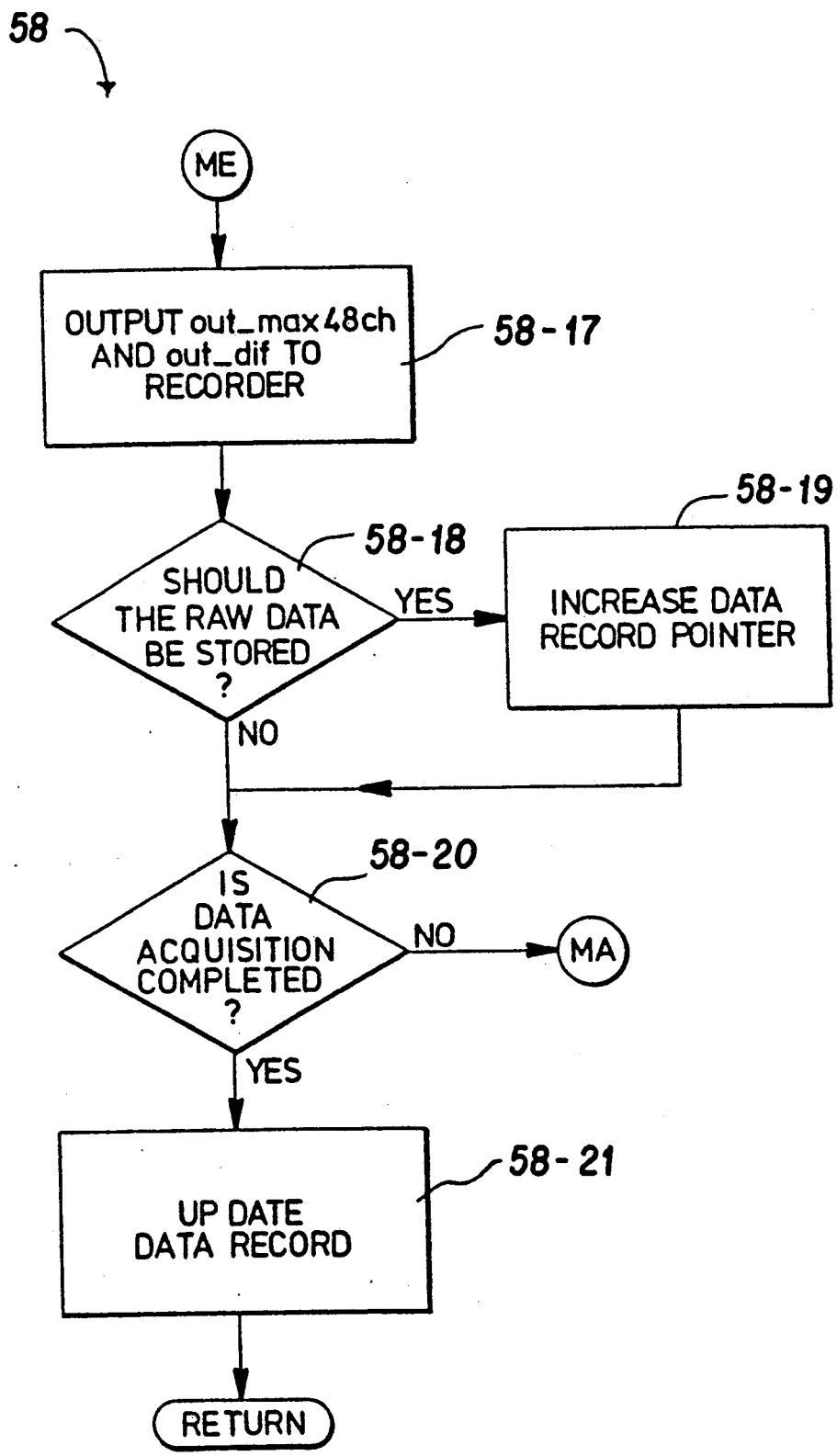

As disclosed herein, the flowchart depicting the preferred program consists of a main program illustrated in FIGS. 6a-c, and six key subroutines illustrated by FIGS. 7a-d, FIG. 8, FIGS. 9a-e, FIG. 10, FIGS. 11a-b, and FIG. 12. A general description of each of these sections is set forth below, followed by a more detailed discussion of the preferred program.

FIGS. 6a-c represent the main program which up the overall framework work for performing the processing tasks necessary to receive, process, and display data as discussed herein. The main program flowchart 56 illustrates the preferred sequence for identifying the various parameters involved in the procedure, allocating sufficient memory to store the necessary data, and assigning a subroutine or other function to be performed by certain function keys and commands.

FIGS. 7a-d set forth flowchart 58 which represents a subroutine identified as "demux_adc". The function of the demux adc program is to enable the computer 18 to receive and store information contained in defect signal 24, circumferential signal 26, and longitudinal signal 28. The preferred program set forth in flowchart 58 is designed to accommodate a defect signal 24 comprising 48 separate channels, corresponding to the 48 defect detectors included in the preferred apparatus.

Figure 8:
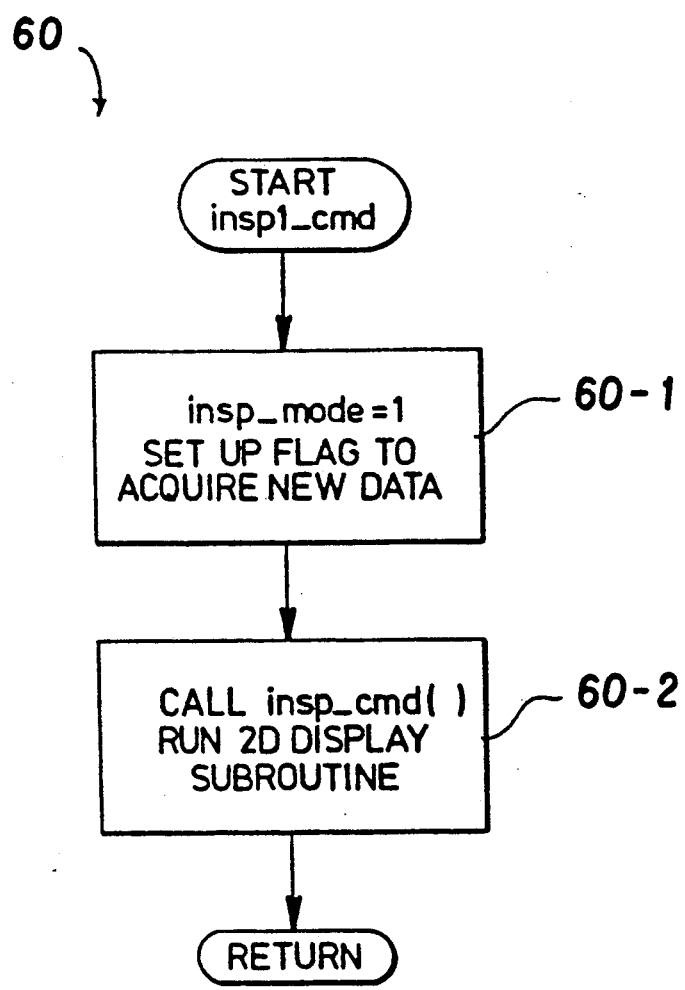
Figure 9A:
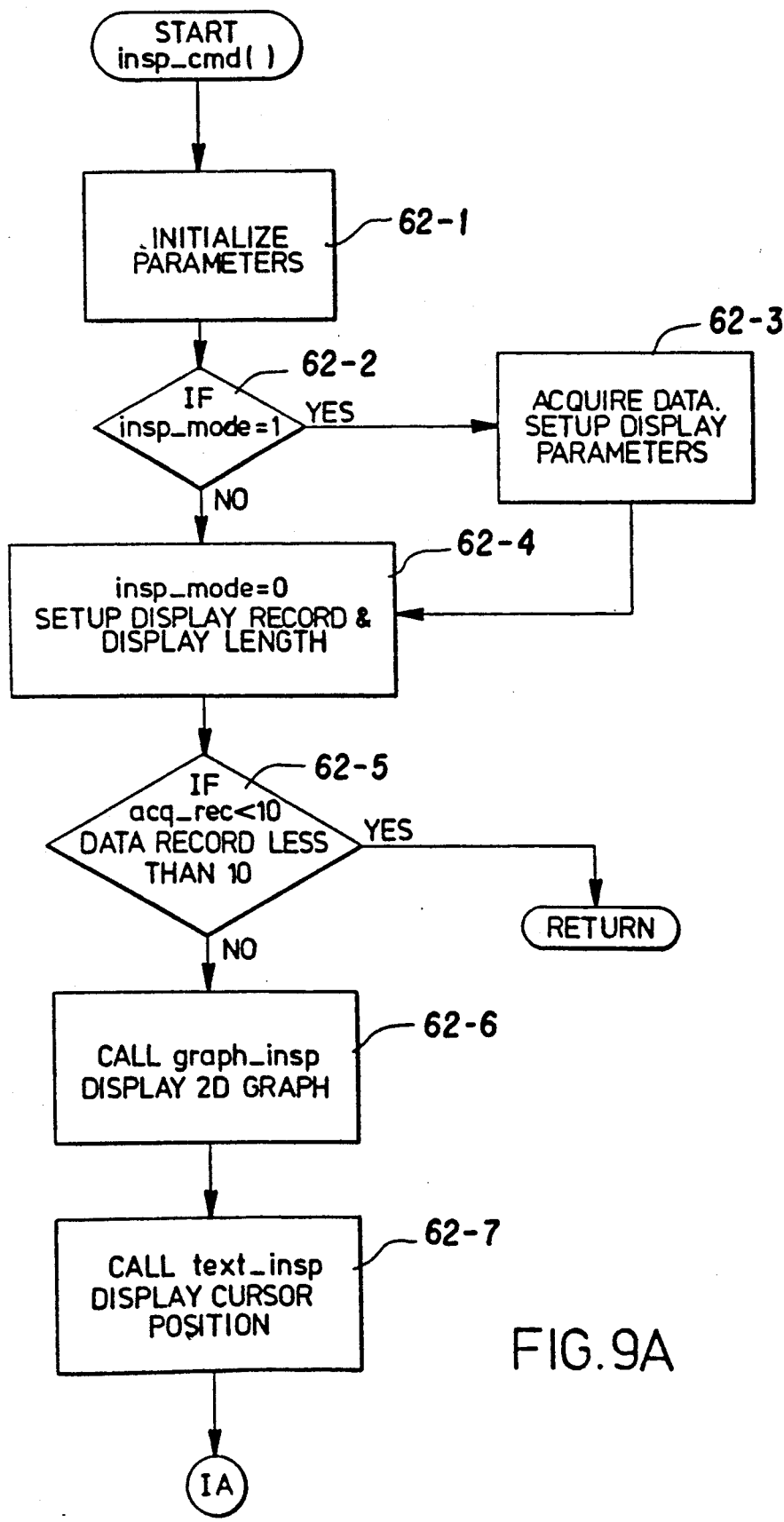
Figure 9B:
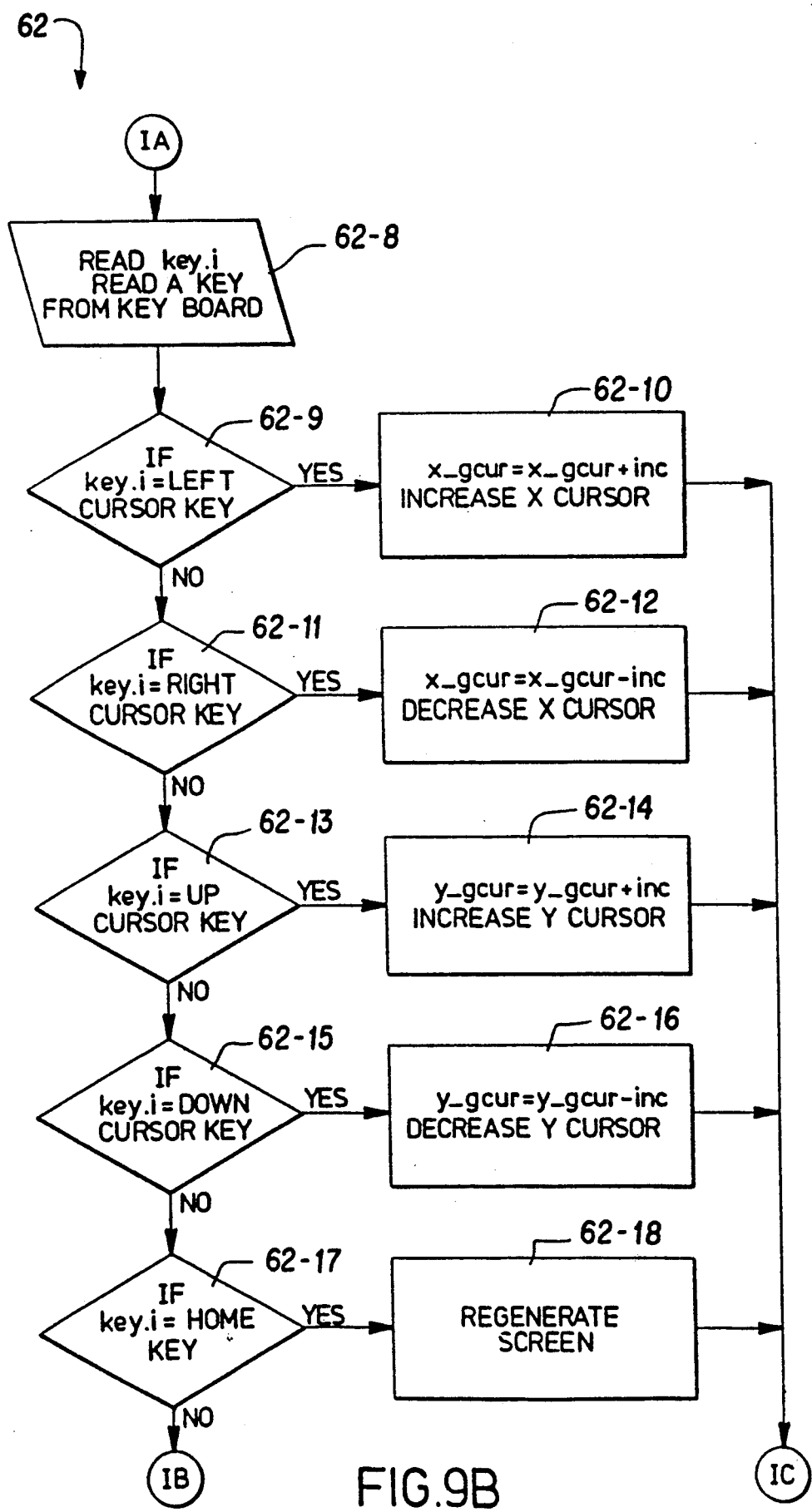
Figure 9C:
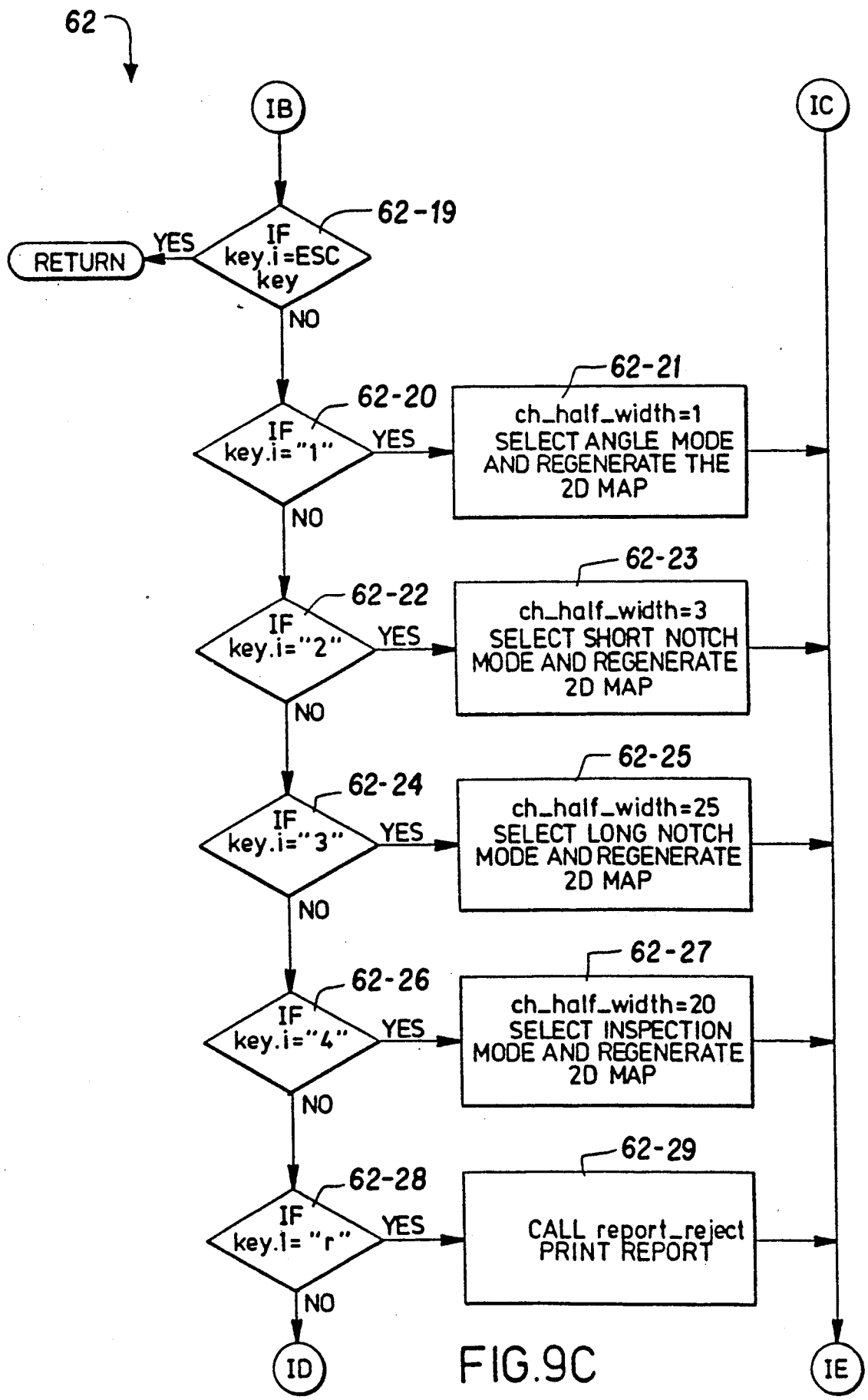
Figure 9D:
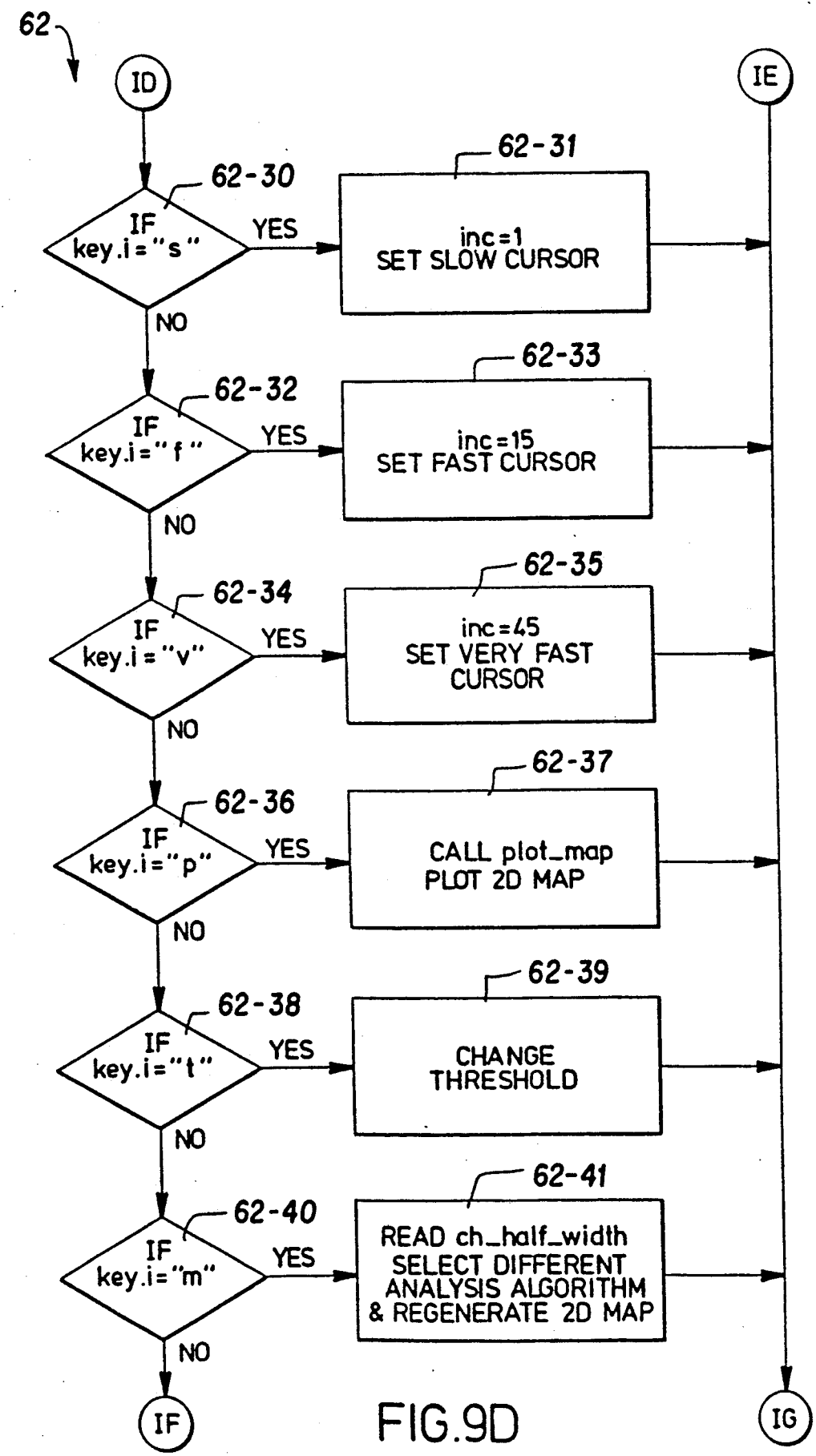
Figure 9E:
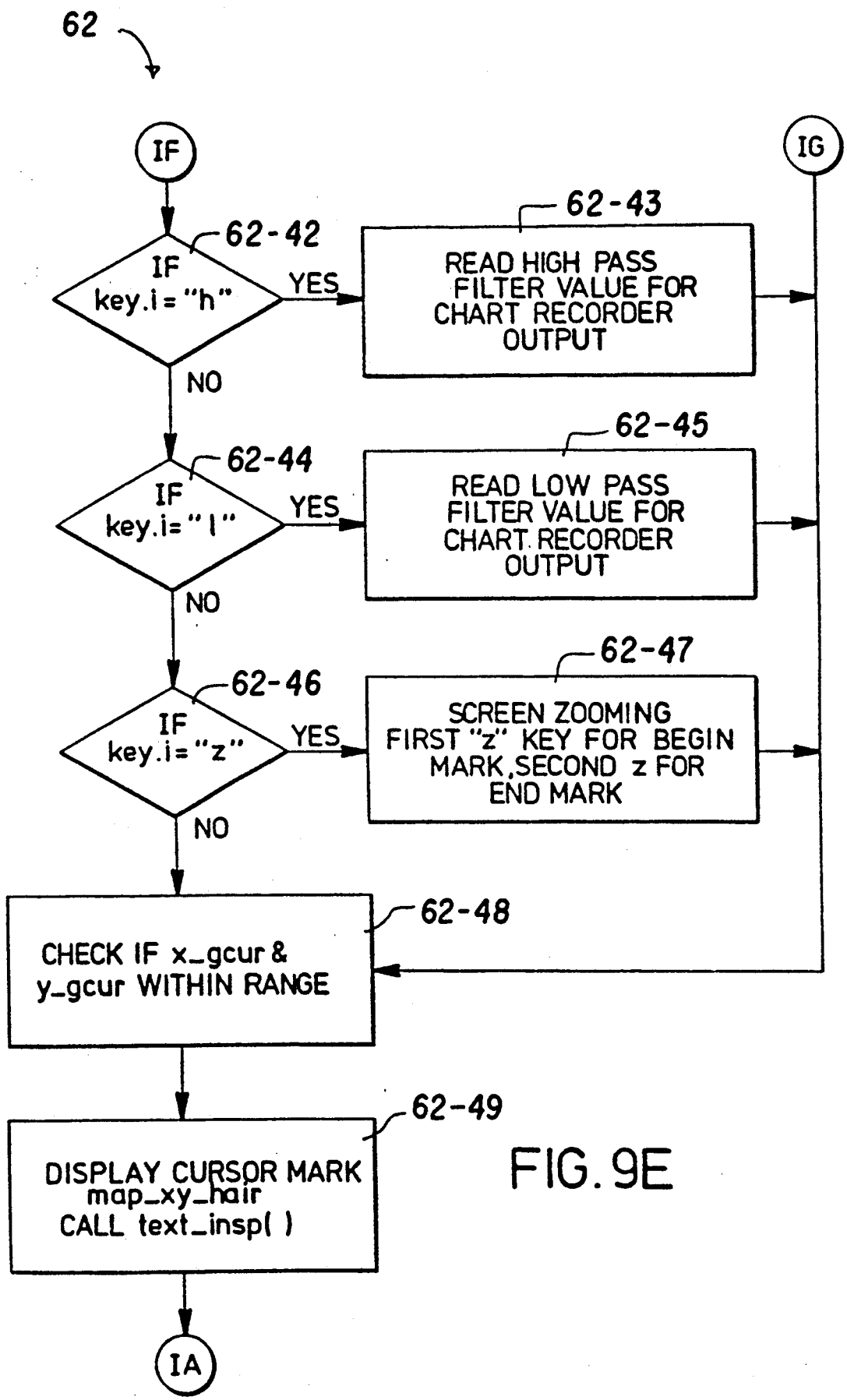

FIG. 8 contains flowchart 60 which represents the "inspl_cmd" (inspection command) subroutine. This subroutine operates to retrieve the defect data from storage and display the data in the inspection mode as illustrated in FIG. 4a and discussed above.

Flowchart 62, as shown in FIGS. 9a-e, discloses a subroutine labeled "insp_cmd()". This portion of the program allows the user of the system to select either short, long, angle, or inspection modes for the two-dimensional display, as discussed above, and also to enhance the display for specified portions when desired. The "insp_cmd()" subroutine utilizes the cursor, appearing as the point of intersection between perpendicular x and y axes, to focus on any given point appearing on the two-dimensional display. By selectively moving the x and y axes so that the cursor coincides with a given defect, the user can determine the precise longitudinal and circumferential position of the defect on the two-dimensional map.

The "insp_cmd()" subroutine identified by flowchart 62 also provides a "screen zooming" feature which yields an enlarged display of a portion of the two-dimensional map, as mentioned above. This feature allows the user to view a particular longitudinal section of tubular member 22 in greater detail simply by designating the longitudinal boundaries of the relevant section. For example, if the user desires to see an exploded view of a central portion of tubular member 22 lying between 10 feet and 20 feet, the user can make appropriate designations at the 10 and 20 foot points and the computer program will expand that portion of the display to fill the entire two-dimensional map.

Figure 10:
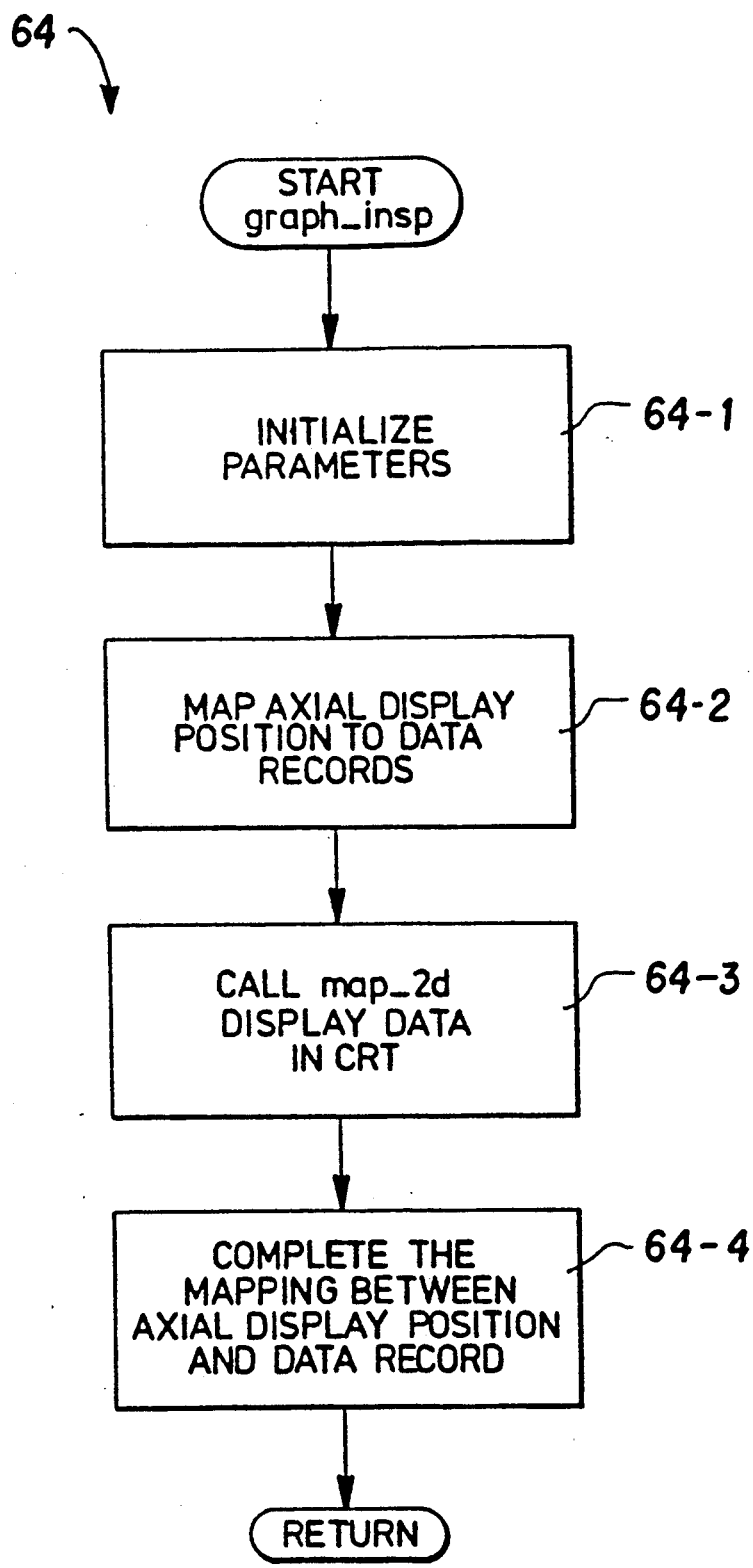

The subroutine entitled "graph_insp", identified by flowchart 64 in FIG. 10, serves the linking function of correlating the longitudinal position of the defect data with the corresponding position on the two-dimensional map for purposes of carrying out "screen zooming". Additionally, this subroutine calls a "map_2d" routine into play to display the defect data on a CRT screen.

Figure 11A:
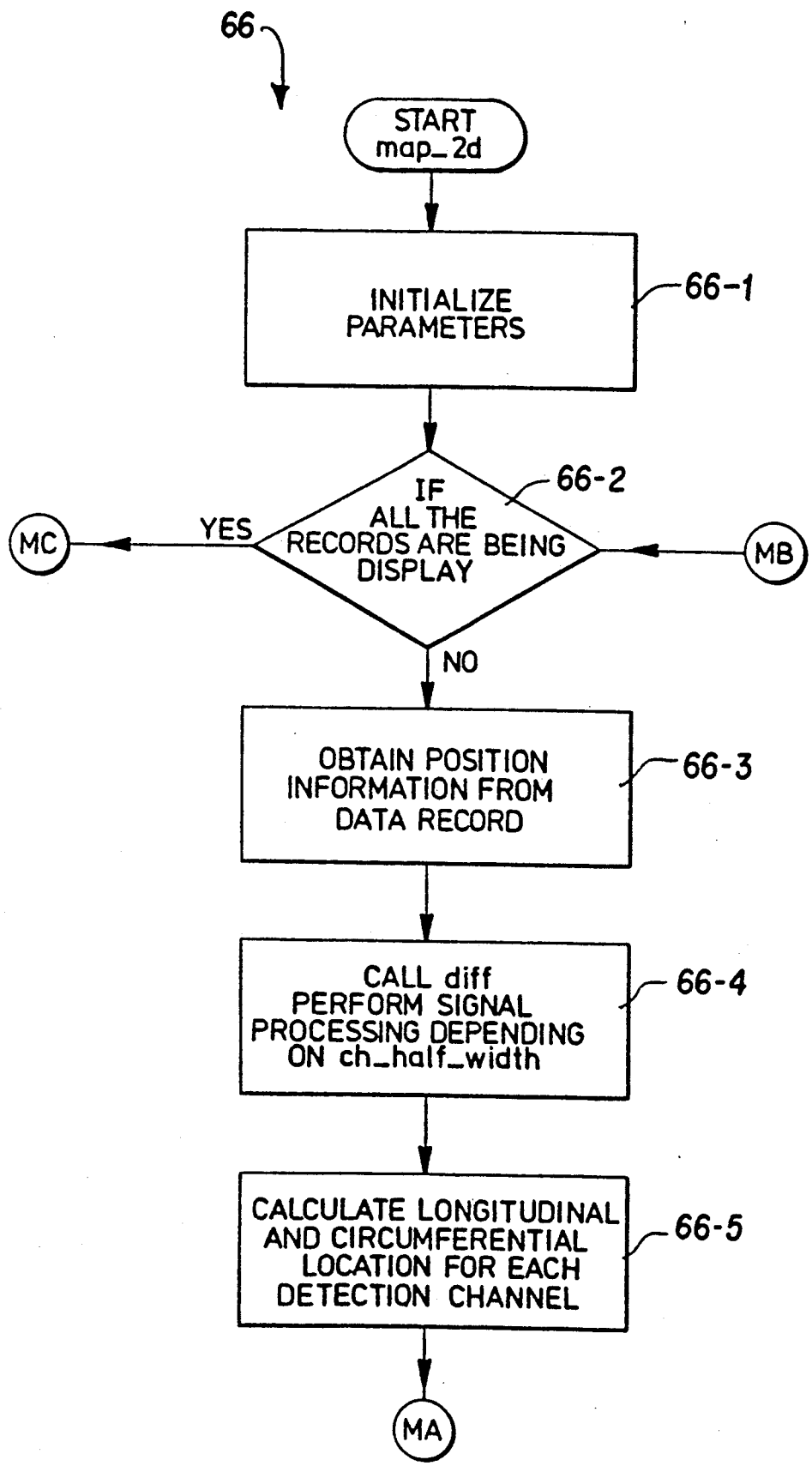
Figure 11B:
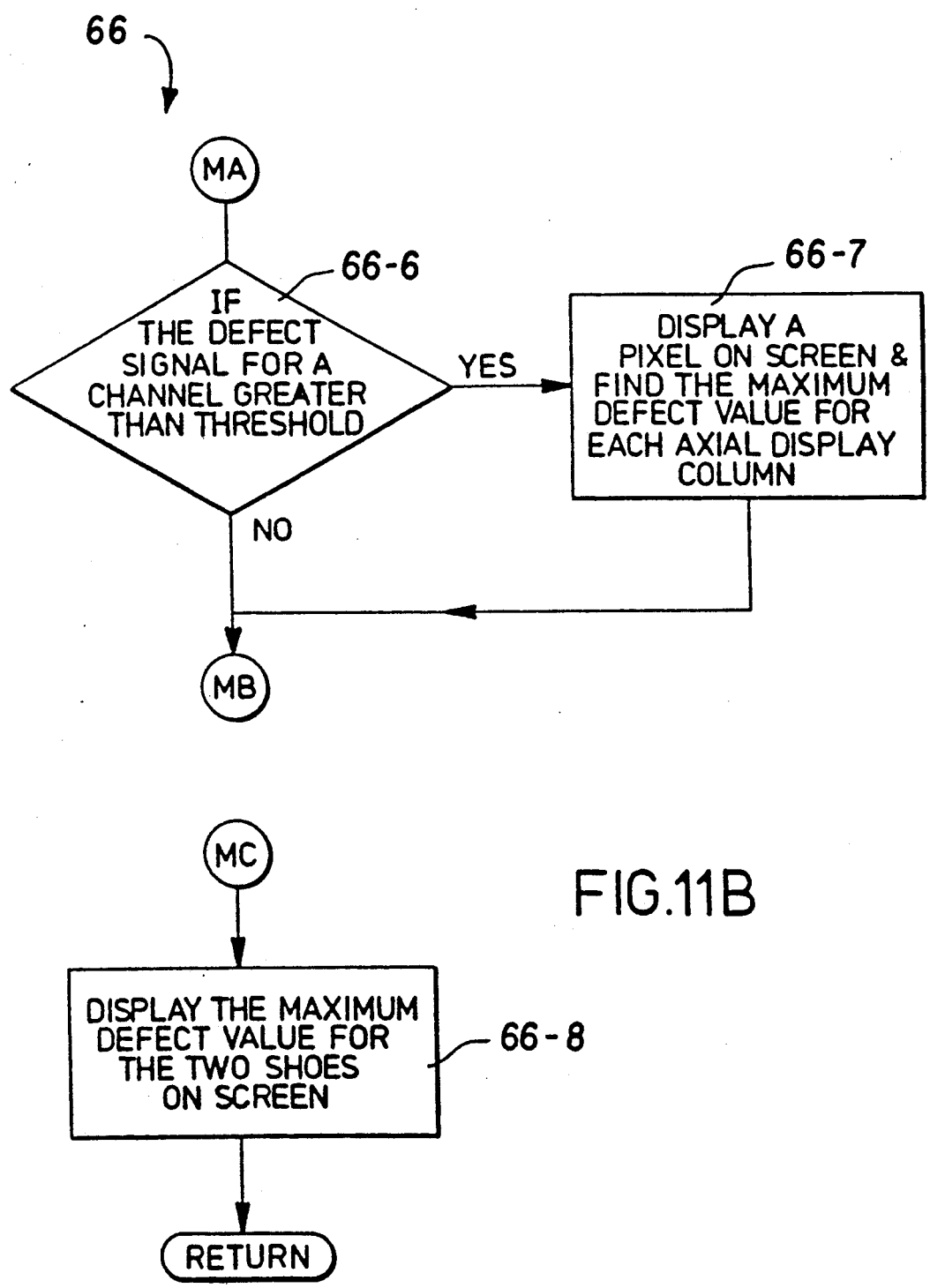

The "map_2d" subroutine mentioned above is disclosed in flowchart 66 illustrated in FIGS. 11a and b. This subroutine operates to correlate the defect, longitudinal, and circumferential signals to determine the position of each defect, and generate a pixel on the CRT screen to visually display each defect in its proper location. When creating the visual display, this subroutine calls upon the "diff" subroutine which adjusts the display according to the mode (short, long, angle, or inspection) selected by the user.

Figure 12:
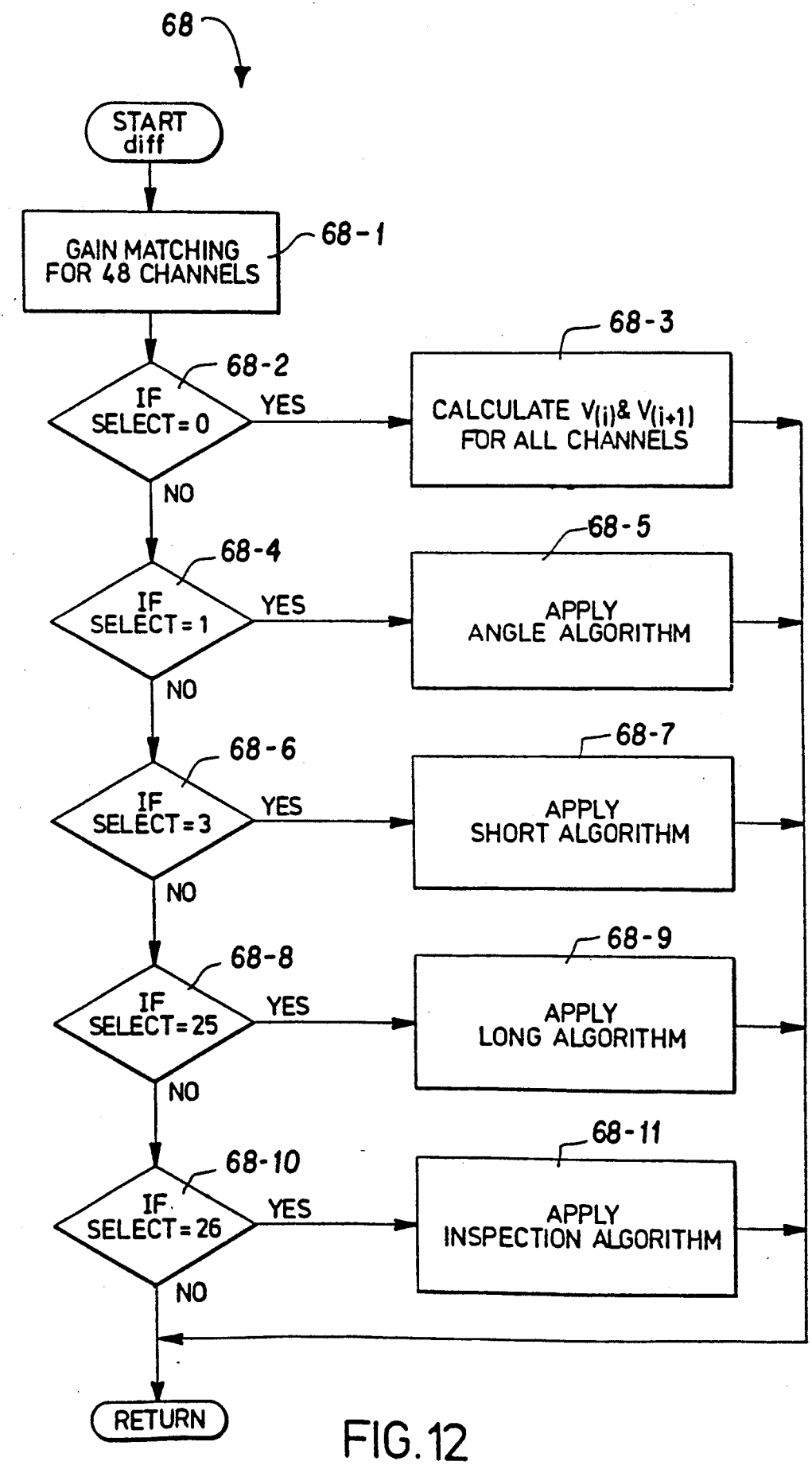

Flowchart 66 illustrated in FIG. 12 sets forth the framework for the "diff" subroutine mentioned above. This subroutine performs the signal processing functions necessary to distinguish the various types of defects based upon size and angular orientation, thus providing for the different display modes discussed herein.

DETAILED DESCRIPTION OF COMPUTER PROGRAM

In order to carry out the principles of the present invention utilizing the preferred program for this purpose, identified schematically as flowchart 56, the first step is to initialize the parameters governing the process (box 56-1). At this stage in the inspection procedure, the user establishes the various operating frequencies and threshold values needed for subsequent calculations. Also established at this stage are the pipe speed, detector gain, inspection head rotational velocity, and the length, outside diameter, and wall thickness of the pipe to be inspected. After all necessary operating parameters have been established, a sufficient block of memory is allocated to store the real time data input from signals 24, 26, and 28 (box 56-2).

Once the internal functions and parameters have been initialized and the memory is properly allocated, the main program instructs the computer to run various subroutines and functions in response to certain entries (box 56-3). The operations automatically performed upon selection of function keys F1–F10 are assigned as follows:

F1 calls the inspl_cmd subroutine, displayed in FIG. 8 as flowchart 60, which assigns a flag value to indicate the acquisition of new data and further calls the insp$_{613}$ cmd() subroutine for generating the two-dimensional display (boxes 56-4 and 56-5);

F2 calls a dsp_cmd subroutine which simply displays the raw real time data (boxes 56-6 and 56-7);

F3 calls the inspl_cmd subroutine, illustrated as flowchart 60 in FIG. 8 which generates the two-dimensional display map for inspection (boxes 56-8 and 56-9);

F4 calls a para_cmd subroutine which allows the user to change the parameters as desired (56-10 and 56-11);

F5 calls an rpm_cmd subroutine which displays the rotational velocity of the rotating inspection head 12 (56-12 and 56-13);

F6 calls the det_offset_cmd subroutine which allows the user to set the required offset for each detector channel (56-14 and 56-15);

F7 calls a set ch_cmd subroutine which allows the user to select the multiplexer output value for each detector channel (boxes 56-16 and 56-17);

F8 calls a set_samp_phres_cmd subroutine which allows the user to set the sampling threshold (boxes 56-18 and 56-19);

F9 calls the save_cmd subroutine which operates to save the data received through input signals 24, 26 and 28 (boxes 56-20 and 56-21);

F10 calls the help_cmd subroutine which generates a help menu on the screen (boxes 56-22 and 56-23);

"Read" command calls the read_cmd subroutine which allows the user to read raw data directly from the file (boxes 56-24 and 56-25);

"DOS" command sets the computer up to perform conventional DOS commands (boxes 56-26 and 56-27); and the "ESCAPE" key returns the computer to DOS format (box 56-28).

The order of the steps performed by the main program illustrated in flowchart 56 constitutes a convenient, logical progression for creating the framework for the overall programming including all subroutines. It will be understood by those skilled in the art, however, that the precise order of steps is, in many instances, simply a matter of choice, and may be rearranged considerably without departing from the teachings of the present invention.

The demux_adc subroutine, illustrated by flowchart 58 in FIGS. 7a–d, constitutes the heart of the signal processing features, wherein signals 24, 26, and 28 are received and stored. As with virtually any computer program, the first step comprises initializing the parameters necessary for performing the operations specified by the remainder of the subroutine (box 58-1). In addition to the parameters previously selected for the main program, the demux_adc subroutine further requires the initialization of the values corresponding to revolution counter signal 26a and angle counter signal 26b (box 58-2).

The demux_adc subroutine next directs the computer to read the defects signal 24 for each of the 48 detector channels, with gain and offset balanced (box 58-3), as well as revolution counter signal 26a, angle counter signal 26b, and longitudinal signal 28 (box 58-4). The period of rotation for inspection head 12 is then established by determining the angle counter reading corresponding to a single revolution of the tool trip head 12 (boxes 58-5 and 58-6).

The demux$_{613}$ adc subroutine then performs the signal processing functions necessary for the real time screen output and chart recorder output. Initially, the maximum value of the forty-eight channels comprising defect signal 24 is determined (box 58-7) and processed by a digital high pass filter (box 58-8). If the maximum value is less than threshold value, the output maximum value (out_max 48 ch) is set at zero (boxes 58-9 and 58-10). The signal difference for each flux detector is then established (boxes 58-11 and 58-12), with the maximum value being processed by a digital band pass filter (box 58-13). If the resulting value (out_dif) is less than a given threshold, the value is set at zero (boxes 58-14 and 58-15).

After the out$_{613}$ max48ch and out$_{613}$ dif parameters have been determined, the amplitude of out_dif is displayed on the CRT screen in real time (box 58-16), and the values of both parameters are converted into analog signals and sent to a two channel strip chart recorder (box 58-17). The computer then determines if the raw data should be stored or discarded (boxes 58-18 and 58-19), and the data acquisition sequence is continued, if necessary, with the data record being updated accordingly (boxes 58-20 and 58-21).

The inspl_cmd subroutine referred to above is identified by flowchart 60 set forth in FIG. 8. This subroutine serves initially to assign a value of 1 to the insp_mode variable "inspect mode", and create a flag to signal the acquisition of new data (box 60-1). This is a preliminary step essential to the operation of the insp_cmd() subroutine, which is also called into play by the inspl_cmd subroutine (box 60-2) as set forth in more detail below.

The insp_cmd(), identified generally as subroutine 62, requires that additional parameters be initialized before performing the operation specified therein (box 62-1). Next, relying upon an instruction previously supplied by the inspl$_{613}$ cmd subroutine, new data is automatically acquired if the insp_mode value equals 1 (boxes 62-2 and 62-3). Regardless of whether or not new data is acquired, the insp_mode is reset to zero and a suitable display record is set up to indicate the length of tubing corresponding to the required data (box 62-4). The computer next determines if all the acquired data records ("acq_rec") have been received and, if not, the user is instructed to depress the F1 key to acquire new data (box 62-5). If all data has been received, the graph_insp subroutine is called to generate a two-dimensional map and display the records thereon (box 62-6).

The next series of operations performed by the insp_cmd() subroutine provide the on-screen focusing feature which allows the user to pinpoint the location of the defects appearing on the two-dimensional map. After all the data is properly displayed on the two-dimensional display, the text_insp subroutine is called and the cursor position is shown as the intersection between x and y axes (box 62-7). The user is then able to accurately position the cursor by moving the x and y axes by depressing the correct key on the keyboard (box 62-8).

In the preferred embodiment illustrated, the "left cursor" key serves to move the x axis left (boxes 62-9 and 62-10), the "right cursor" key moves the x axis right (boxes 62-11 and 62-12), the "up cursor" key moves the y axis upwardly (boxes 62-13 and 62-14) and the "down cursor" key moves the y axis downwardly (boxes 62-15 and 62-16). Finally, the user has the option of regenerating the screen simply by depressing the "HOME" key (boxes 62-17 and 62-18), or exiting the subroutine by depressing the "ESCAPE" key (box 62-19).

The insp_cmd() subroutine allows the user to vary the display mode between short, long, angle, and inspection modes, and regenerate the two-dimensional map accordingly, as discussed above. The program assigns a numerical entry corresponding to each different mode, as follows: if the numeral "1" is entered, the two-dimensional map is regenerated in the angle mode (boxes 62-20 and 62-21); if the numeral "2" is entered, the map is regenerated in the short mode (boxes 62-22 and 62-23); if the numeral "3" is entered, the map is regenerated in the long mode (boxes 62-24 and 62-25); and if the numeral "4" is entered, the map is regenerated in the inspection mode (boxes 62-26 and 62-27).

This subroutine also assigns functions to various letters of the alphabet to provide additional features which may be helpful to the user of the system. As illustrated, the selection of the letter "R" calls a report_reject subroutine which generates the defect summary shown in FIG. 5 (boxes 62-28 and 62-29). Selection of the letters "S", "F", or "V" varies the speed of the cursor movement from slow, to fast, to very fast, respectively (boxes 62-30 through 62-35).

Selection of the letter "P" instructs the computer to plot the two-dimensional display map on an attached plotter (boxes 62-36 and 62-37). If the user desires to change the threshold value to increase or decrease the amount of information being displayed, the letter "T" may be selected (boxes 62-38 and 62-39). Entry of the letter "M" allows the user to select a completely different analysis algorithm, assign a corresponding channel half width value ($ch_{613}$ half$_{613}$ width), and regenerate the two-dimensional display map in accordance with the new algorithm (boxes 62-40 and 62-41).

The user of system 10 can quickly check the high pass and low pass filter values for the digital filters included in the chart recorder output by entering either the letter "H" or "L", respectively (boxes 62-42 through 62-45). Finally, by entering the letter "Z", the user can utilize the screen zooming feature discussed above, wherein the first "Z" entry marks the initial longitudinal boundary and the second "Z" entry marks the final longitudinal boundary for the enlarged view (boxes 62-46 and 62-47).

In order to avoid confusion and erroneous displays, the insp_cmd() subroutine automatically checks the positions of the x and y axes to insure that both are within the range of the two-dimensional display shown on the screen (box 62-48). In the event that one or more of the previously described functions has been performed, thus temporarily removing the two-dimensional display map, the cursor is then re-displayed as the intersection of x and y axes (box 62-49).

The graph$_{613}$ insp subroutine referenced at box 62-6 is illustrated as flowchart 64 in FIG. 10. Additional parameters must first be initialized (box 64-1) in order for the computer to perform the correlating functions of this subroutine. After the necessary parameters have been established, the axial, or longitudinal, display positions on the CRT screen are correlated to the defect data points contained in the data records for purposes of the screen zooming feature discussed above (box 64-2). After this correlation, or mapping, procedure has begun, the map_2d subroutine is called upon to display the data on the CRT screen (box 64-3) while the correlation continues until completed (box 64-4).

The map_2d subroutine referred to illustrated as flowchart 66 in FIGs. 11*a* and *b*. As with certain other subroutines, this portion of the program requires that new parameters be initialized before any additional processing is performed (box 66-1). The processing functions of this subroutine are essentially contained within a logic loop, wherein the computer first determines if all the records are being displayed (box 66-2), and, if so, the maximum defect value for each of the two detector head segments 13 is displayed on the screen (box 66-8).

If the computer determines that all records are not yet being displayed, it proceeds by first obtaining additional position information from the data records (box 66-3). The diff subroutine is next called upon to apply suitable algorithms to the raw data, thus generating four sets of distinctive values, with each set corresponding to one of the four display modes, short, long, angle, or inspection (box 66-4). The longitudinal and circumferential location for each of the forty-eight detector channels are next determined by correlating signals 24, 26, and 28 (box 66-5).

The predetermined threshold value for the particular display mode selected is compared to each numerical value comprising defect signal 24 and, if the signal value is greater than the threshold value, a pixel is displayed on the CRT screen for the maximum defect value for each longitudinal position along the length of tubular member 22, as displayed on the two-dimensional map (boxes 66-6 and 66-7). If, on the other hand, the defect signal value is less than the threshold value, the signal value is ignored and the logic loop repeated.

The final key portion of the preferred program for this invention is the diff subroutine identified by flowchart 68 in FIG. 12. Since the function of this program is to process all numerical values contained within defect signal 24, it is imperative that the gain setting be matched for each of the forty-eight channel corresponding to the forty-eight separate flux detectors (box 68-1). The computer then performs one of five possible calculations depending upon the channel half width selected by the user.

If the selection is "0", the voltages for all channels are calculated for each discrete solid segment of tubular member 22 (boxes 68-2 and 68-3). If, however, a channel half width of 1, 3, 25, or 26 is selected, the voltage values are processed according to the angle algorithm, short algorithm, long algorithm, or inspection algorithm, respectively, to generate the distinctive values needed to produce the four different display modes discussed above (boxes 68-4 through 68-11).

The precise programming steps required to reproduce the preferred embodiment of the present invention will become apparent to those skilled in the art upon disclosure of the flowchart and the remainder of the specification set forth herein. It should also be understood this specification is by illustration only and that the invention is not necessarily limited to the specific embodiment disclosed herein, since alternative embodiments and operating techniques will become apparent to those skilled in the art in view of the disclosure.

Accordingly, modifications are contemplated which can be made without departing from the spirit of the described invention.

What I claim is:

1. A method of mapping a plurality of defects of differing shapes, lengths, and angular orientations in a tubular member having a plurality of discrete solid segments, the sum of which comprise the entire solid volume of said tubular member, comprising the steps of:

generating at least one defect signal representing a defect in at least one discrete solid segment of said tubular member for each of said plurality of defects, each of said at least one defect signal having an amplitude value;

generating a longitudinal signal indicating the longitudinal position of said at least one discrete solid segment of said tubular member;

generating a circumferential signal indicating the circumferential position of said at least one discrete solid segment of said tubular member;

correlating said defect, longitudinal, and circumferential signals to obtain defect data, said defect data including the longitudinal position and circumferential position of said defect in said at least one discrete solid segment of said tubular member;

displaying the presence of said defect as at least one indication on a two-dimensional map without simultaneous display on said two-dimensional map of said amplitude values of each of said at least one defect signal, said map including:

a first axis corresponding to the length of said tubular member;

a second axis corresponding to the circumference of said tubular member;

wherein the relative number and positions of said indications with respect to said first and second axes indicate location of each of said plurality of defects on said tubular member and further indicate said shape, length, and angular orientation of each of said plurality of defects relative to said tubular members and to each other of said plurality of defects; and wherein said location, shape, length, and angular orientation of each of said plurality of defects relative to said tubular member and relative to others of said plurality of defects is directly measurable from said two-dimensional map, 2. The method of claim 1 wherein said step of generating at least one defect signal comprises:

generating a plurality of said defect signals which collectively represent all defects in said entire solid volume of said tubular member.

3. The method of claim 1 wherein said defect signal, said longitudinal signal, and said circumferential signals comprise analog electrical signals, said method further comprising the step of:

displaying simultaneously said amplitude values of said at least one defect signal separately from said two-dimensional map of said plurality of defects.

4. The method of claim 1 wherein the step of displaying at a display means said defect data comprises:

displaying said defect data such that the different characteristics of said defect are separately identifiable.

5. The method of claim 4 wherein said characteristics are displayed in a table having at least four portions, including:

a first portion for displaying the longitudinal position of said defect, a second portion for displaying the circumferential position of said defect, a third portion for displaying the longitudinal length of said defect, and a fourth portion for displaying the angular orientation of said defect.

6. The method of claim 1 wherein the step of displaying comprises:

displaying said defect data on a visual monitor operative to selectively receive continuously generated electronic pulses and convert said electronic pulses to visual images.

7. The method of claim 1 wherein the step of displaying comprises:

displaying said defect on a chart recorder.

8. The method of claim 1 wherein the step of displaying comprises:

plotting said defect data on a plotter.

9. The method of claim 1 wherein the step of displaying comprises:

printing said defect data on a printer.

10. The method of claim 1 wherein said amplitude of said at least one defect signal is displayed on a display separate from said two-dimensional map, but which is axially aligned with said two-dimensional map.

11. A method of mapping a plurality of defects, according to claim 1, wherein said two-dimensional map is defined by a plurality of pixels, and wherein each of said at least one defect signal represents a pixel on said two-dimensional map.

12. A method of mapping a plurality of defects, according to claim 1, wherein said two-dimensional map is defined by a plurality of pixels, and wherein each of said at least one defect signal constitutes a pixel on said two-dimensional map, and represents the presence of said defect in a particular discrete solid segment of said tubular member.

13. A method of mapping a plurality of defects, according to claim 1, wherein said plurality of defects are classified into a plurality of differing types of defects, and wherein said step of displaying comprises selectively displaying only a selected one of said plurality of differing types of defects.

14. A method of mapping a plurality of defects, according to claim 1, wherein said plurality of defects include a plurality of defects of differing lengths and said tubular member has a longitudinal central axis, and wherein said step of displaying comprises:

selectively displaying the presence of said defect as at least one indication on a two-dimensional map having a first axis corresponding to said longitudinal central axis of said tubular member in one of a plurality of alternative modes including a length of defect mode in which only a subset of defects of predetermined length value are emphasized on said two-dimensional map and all other defects are not emphasized.

15. A method of mapping a plurality of defects, according to claim 1, wherein said plurality of defects include a plurality of defects of differing lengths, and wherein said step of displaying comprises:

selectively displaying the presence of said defect as at least one indication on a two-dimensional map having a first axis corresponding to the length of said tubular member and a second axis corresponding to the circumference of said tubular member in the following alternative modes;
- a long defect mode in which only defects having a length above a predetermined length value are emphasized on said two-dimensional map and all other defects are not emphasized; and
- a short defect mode in which only defects having a shortness below a predetermined length value are emphasized on said two-dimensional map and all other defects are not emphasized.

16. A method of mapping a plurality of defects, according to claim 1, wherein said plurality of defects include a subset of angular defects out of axial alignment with the longitudinal central axis of said tubular member by a predetermined angular threshold, wherein the step of displaying comprises:
   selectively displaying the presence of said defect as at least one indication on a two-dimensional map having a first axis corresponding to said central longitudinal axis of said tubular member and a second axis corresponding to the circumference of said tubular member in one of a plurality of alternative modes, including an angular defect mode in which only said subset of angular defects out of axial alignment with said central longitudinal axis by said predetermined angular value are emphasized on said two-dimensional map and all other defects are not emphasized.

17. A method of mapping a plurality of defects, according to claim 1, wherein said plurality of defects include a first subset of long defects having a length above a predetermined length value, a second subset of short defects having a length below a predetermined shortness value, and a third subset of angular defects out of axial alignment with the longitudinal central axis of said tubular member by a predetermined angular value, wherein the step of displaying comprises:
   selectively displaying the presence of said defect as at least one indication on a two-dimensional map having a first axis corresponding to said central longitudinal axis of said tubular member and a second axis corresponding to the circumference of said tubular member in the following alternative modes:
   - a long defect mode in which only said first subset of long defects having a length above said predetermined length value are emphasized on said two-dimensional map and all other defect types are not emphasized;
   - a short defect mode in which only said second subset of short defects having a length below said predetermined shortness value are emphasized on said two-dimensional map and all other defect types are not emphasized; and
   - an angle defect mode in which only said third subset of angular defects out of axial alignment with said longitudinal central axis by said predetermined angular value are emphasized on said two-dimensional map and all other defect types are not emphasized.

18. A method of mapping a plurality of defects, according to claim 1, wherein said plurality of defects include a first subset of long defects having a length above a predetermined length value, a second subset of short defects having a length below a predetermined shortness value; and a third subset of angular defects out of axial alignment with the longitudinal central axis of said tubular member by a predetermined angular value, wherein the step of displaying comprises:
   selectively displaying the presence of said defect as one or more indications on a two-dimensional map having a first axis corresponding to said central longitudinal axis of said tubular member and a second axis corresponding to the circumference of said tubular member in the following alternative modes:
   - a long defect mode in which only said first subset of long defects having a length above said predetermined length value are emphasized on said two-dimensional map and all other defect types are not emphasized;
   - a short defect mode in which only said second subset of short defects having a length below said predetermined shortness value are emphasized on said two-dimensional map and all other defect types are not emphasized;
   - an angle defect mode in which only said third subset of angular defects out of axial alignment with said longitudinal central axis by said predetermined angular value are emphasized on said two-dimensional map and all other defect types are not emphasized; and
   - a full defect mode in which said first subset of long defects, said second subset of short defects, and said third subset of angular defects are simultaneously displayed and emphasized on said two-dimensional map.

19. A method of mapping a plurality of defects, according to claim 1, wherein said step of generating at least one defect signal comprises:
   providing an inspection means including a plurality of flux detecting coils;
   generating a magnetic flux in said tubular member;
   detecting with said plurality of flux detecting coils said magnetic flux in a plurality of discrete solid members said tubular member;
   producing from said detected magnetic flux at least one signal representing a defect in at least one discrete solid segment of said tubular member for each of said plurality of defects, each of said at least one defect signal having an amplitude value; and
   recording said amplitude value for each of said at least one defect signal.

20. A method of mapping a plurality of defects, according to claim 1, wherein said plurality of defects include a plurality of differing types of defects, and wherein said step of generating at least one defect signal comprises:
   providing a computer with memory and an inspection means including a plurality of flux detecting coils;
   generating a magnetic flux in said tubular member;
   detecting with said plurality of flux detecting coils said magnetic flux in a plurality of discrete solid members of said tubular member;
   producing from said detected magnetic flux at least one signal representing a defect in at least one discrete solid segment of said tubular member for each of said plurality of defects, each of said at least one defect signal having an amplitude value;
   recording into computer memory said amplitude value for each of said at least one defect signal; and
   wherein said method further comprises:
   distinguishing with said computer said plurality of differing types of defects.

21. A method of mapping a plurality of defects, according to claim 1, wherein said step of generating at least one defect signal comprises:
providing an inspection means including a plurality of flux detecting coils;
generating a magnetic flux in said tubular member;
detecting with said plurality of flux detecting coils said magnetic flux in a plurality of discrete solid members of said tubular member;
producing from said detected magnetic flux at least one signal representing a defect in at least one discrete solid segment of said tubular member for each of said plurality of defects, each of said at least one defect signal having an amplitude value;
recording said amplitude value for each of said at least one defect signal; and
wherein said step of displaying further comprises:
selecting at least one signal threshold;
comparing said at least one signal threshold to said amplitude value of each of said at least one defect signal to create a subset of datapoints ready for display; and
displaying only said subset of datapoints to indicate the presence of said plurality of defects on said two-dimensional map.

22. A method of mapping a plurality of defects, according to claim 1, wherein said step of generating at least one defect signal comprises:
providing a computer with memory and an inspection means including a plurality of flux detecting coils;
generating a magnetic flux in said tubular member;
detecting with said plurality of flux detecting coils said magnetic flux in said tubular member;
producing from said detected magnetic flux at least one signal representing a defect in at least one discrete solid segment of said tubular member for each of said plurality of defects, each of said at least one defect signal having an amplitude value;
recording said amplitude value for each of said at least one defect signal in said memory of said computer; and
wherein said step of displaying further comprises:
selecting with said computer at least one signal threshold;
comparing with said computer said at least one signal threshold to said amplitude value of each of said at least one defect signal to create a subset of datapoints ready for display; and
displaying only said subset of datapoints to indicate the presence of said plurality of defects on said two-dimensional map.

23. A method of mapping a plurality of defects, according to claim 1, further comprising:
selectively displaying only a portion of said two-dimensional map.

24. A method of mapping a plurality of defects, according to claim 1, further comprising:
selectively displaying only a portion of said two dimensional map; and
simultaneously enlarging said portion of said two-dimensional map.

25. A method for mapping defects in a tubular member having a longitudinal central axis, said defects including a first subset of long defects having a length above a predetermined length value, a second subset of short defects having a length below a predetermined shortness value, and a third subset of angular defects out of axial alignment with said longitudinal central axis by a predetermined angular value, comprising the steps of:
generating a first signal corresponding to each of said defects;
generating a second signal corresponding to the longitudinal position of each of said defects;
generating a third signal corresponding to the circumferential position of each of said defects;
correlating said first signal with said second signal and said third signal to obtain defect data, said defect data including the longitudinal position and circumferential position of each of said defects; and
selectively displaying the presence of said defect as at least one indication on a two-dimensional map having a first axis corresponding to the longitudinal central axis of said tubular member and a second axis corresponding to the circumference of said tubular member in the following alternative modes;
a long defect mode in which only said first subset of long defects having a length above said predetermined length value are emphasized on said two-dimensional map and all other defect types are not emphasized;
a short defect mode in which only said second subset of short defects having a length below said predetermined shortness value are emphasized on said two-dimensional map and all other defect types are not emphasized;
an angle defect mode in which only said third subset of angular defects out of axial alignment with said longitudinal central axis by said predetermined angular value are emphasized on said two-dimensional map and all other defect types are not emphasized;
a full defect mode in which said first subset of long defects, said second subset of short defects, and said third subset of angular defects are simultaneously displayed on said two-dimensional map.

26. The method of claim 25 wherein said step of selectively displaying further comprises:
selectively generating a table having at least four portions, including:
a first portion for displaying the longitudinal position of each of said defects;
a second portion for displaying the circumferential position of each of said defects;
a third portion for displaying the longitudinal length of each of said defects; and
a fourth portion for displaying the angular orientation of each of said defects.

27. The method of claim 25, further comprising:
converting said first signal corresponding to each of said defects to a series of numerical values including a first portion representing said defects and a second portion representing non-defect characteristics;
selecting a threshold number; and
comparing said numerical values to said threshold number to identify said first portion thereof.

28. A method of mapping a plurality of defects, according to claim 25, wherein said two-dimensional map is defined by a plurality of pixels, and wherein each of said at least one defect signal represents a pixel on said two-dimensional map.

29. A method of mapping a plurality of defects, according to claim 25, wherein said two-dimensional map is defined by a plurality of pixels, and wherein each of said at least one defect signal constitutes a pixel on said two-dimensional map, and represents the presence of said defect in a particular discrete solid segment of said tubular member.

30. A method of mapping a plurality of defects, according to claim 25, wherein said step of generating a first signal comprises:
   providing an inspection means including a plurality of flux detecting coils;
   generating a magnetic flux in said tubular member;
   detecting with said plurality of flux detecting coils said magnetic flux in said tubular members;
   producing from said detected magnetic flux at least one defect signal representing a defect in at least one discrete solid segment of said tubular member for each of said plurality of defects, each of said at least one defect signal having an amplitude value; and
   recording said amplitude value for each of said at least one defect signal.

31. A method of mapping a plurality of defects, according to claim 25, wherein said step of generating a first signal comprises:
   providing an inspection means including a plurality of flux detecting coils;
   generating a magnetic flux in said tubular member;
   detecting with said plurality of flux detecting coils said magnetic flux in said tubular member;
   producing from said detected magnetic flux at least one defect signal representing a defect in at least one discrete solid segment of said tubular member for each of said plurality of defects, each of said at least one defect signal having an amplitude value;
   recording said amplitude value for each of said at least one defect signal; and
wherein said step of displaying further comprises:
   selecting at least one signal threshold;
   comparing said at least one signal threshold to said amplitude value of each of said at least one defect signal to create a subset of datapoints ready for display; and
   displaying said subset of datapoints to indicate the presence of said plurality of defects on said two-dimensional map.

32. A method of mapping a plurality of defects, according to claim 25, wherein said step of generating a first signal comprises:
   providing a computer with memory and an inspection means including a plurality of flux detecting coils;
   generating a magnetic flux in said tubular member;
   detecting with said plurality of flux detecting coils said magnetic flux in said tubular member;
   producing from said detected magnetic flux at least one defect signal representing a defect in at least one discrete solid segment of said tubular member for each of said plurality of defects, each of said at least one defect signal having an amplitude value;
   recording said amplitude value for each of said at least one defect signal in said memory of said computer; and
wherein said step of displaying further comprises:
   selecting with said computer at least one signal threshold;
   comparing with said computer said at least one signal threshold to said amplitude value of each of said at least one defect signal to create a subset of datapoints ready for display; and
   displaying said subset of datapoints to indicate the presence of said plurality of defects on said two-dimensional map.

33. A method of mapping a plurality of defects, according to claim 25, wherein said plurality of defects include a plurality of differing types of defects including a first subset of long defects, a second set of short defects, and a third subset of angular subset defects, and wherein said step of generating said first signal;
   providing a computer memory and an inspection means including a plurality of flux detecting coils;
   generating a magnetic flux in said tubular member,
   detecting with said plurality of flux detecting coils said magnetic flux in said tubular member;
   producing from said detected magnetic flux at least one defect signal representing a defect in at least one discrete solid segment of said tubular member for each of said plurality of defects, each of said at least one defect signal having an amplitude value; and
   recording into computer memory said amplitude value for each of said at least one defect signal; and
wherein said method further comprises:
   distinguishing with said computer said plurality of differing types of defects, including said long, short, and angular defects.

34. A method of mapping a plurality of defects, according to claim 25, further comprising:
   selectively displaying only a portion of said two-dimensional map.

35. A method of mapping a plurality of defects, according to claim 25, further comprising:
   selectively displaying only a portion of said two dimensional map; and
   simultaneously enlarging said portion of said two-dimensional map.

36. An apparatus for mapping a plurality of defects of differing shapes, lengths, and angular orientations in a tubular member having a plurality of discrete segments, comprising:
   means for generating at least one defect signal representing a defect in at least one discrete segment of said tubular member, for each of said plurality of defects, each of said at least one defect signal having an amplitude value;
   means for generating a longitudinal signal indicating the longitudinal position of said at least one discrete segment of said tubular member;
   means for generating a circumferential signal indicating the circumferential position of said at least one discrete segment of said tubular member;
   means for correlating said defect, longitudinal, and circumferential signals to obtain defect data, said defect data including the longitudinal position and circumferential position of said defects in said at least one discrete segment of said tubular member; and
   display means for selectively displaying said defect data on a two-dimensional map independently of said amplitude value of each of said at least one defect signal, said map including:
      a first axis corresponding to the length of said tubular member;
      a second axis corresponding to the circumference of said tubular member;
      wherein the relative number and position of said at least one defect signal with respect to said first and second axes indicate the location, shape, length and angular orientation of each of said plurality of defects relative to said tubular member and relative to others of said plurality of defects, all without regard to said amplitude value of each of said at least one defect signal.

37. The apparatus of claim 36 wherein said means for generating at least one defect signal comprise an electromagnetic inspection apparatus, including:
- at least one driven coil for inducing a magnetic field in said discrete segment of said tubular member,
- at least one pick-up coil for detecting the magnetic field induced by said driven coil, and
- at least one magnetic flux detector, responsive to the variations in said flux caused by defects and generating a signal corresponding thereto.

38. The apparatus of claim 36 wherein said means for generating a longitudinal signal comprise:
- a generally rigid support member disposed adjacent said tubular member;
- a wheel rotatably secured to said support member, wherein the outer perimeter of said wheel is in contact with the outer surface of said tubular member while said apparatus is operating, such that longitudinal movement of said tubular member relative to said apparatus causes corresponding rotational movement of said wheel; and
- signal generating means communicating with said wheel for generating a signal corresponding to the distance traveled by said wheel along the outer surface of said tubular member.

39. The apparatus of claim 36 wherein said means for generating a circumferential signal comprise:
- sensing means for detecting the position of said defect signal generating means relative to said tubular member; and
- means for generating a signal indicating said relative position.

40. The apparatus of claim 39, wherein:
- said defect signal generating means comprise a generally annularly-shaped, rotatable defect detector having an open interior of sufficiently large diameter to allow said tubular member to pass axially therethrough,
- said defect detector being rotatably mounted within said apparatus such that said tubular member is passable through said open interior of said defect detector during rotation thereof; and
- said sensing means comprise:
  - a position indicator rigidly secured to said defect detector and rotatable therewith,
  - a stationary sensor, cooperating with said position indicator, for detecting each revolution of said defect detector and generating a revolution signal indicative thereof,
  - clock means for generating a time signal, and
  - computing means for receiving and correlating said revolution signal and said time signal, and selectively determining the circumferential position of said defect detector relative to said tubular member at any given time.

41. The apparatus of claim 36 wherein said means for correlating said defect, longitudinal, and circumferential signals comprise a computer.

42. The apparatus of claim 36 wherein said display means comprise at least one of the following:
(a) a CRT screen;
(b) a chart recorder;
(c) a plotter; or
(d) a printer.

43. An apparatus for mapping a plurality of defects, according to claim 36, wherein said plurality of defects are classified into a plurality of differing types of defects, and wherein said display means is operable in a plurality of display modes, each for displaying a different type of defect.

44. An apparatus for mapping a plurality of defects, according to claim 36, wherein said display means includes:
- means for selectively displaying each of said plurality of defects as at least one indication on said two-dimensional map in one of a plurality of alternative modes including a length defect mode in which only a subset of defects of predetermined length value are displayed and emphasized on said two-dimensional map and all other defects are not emphasized.

45. An apparatus for mapping a plurality of defects, according to claim 36, wherein said plurality of defects include a plurality of defects of differing lengths, and wherein said display means further includes:
- means for selectively displaying the presence of said defect as at least one indication on said two-dimensional map in the following alternative modes:
  - a long defect mode in which only defects having a length above a predetermined length value are emphasized on said two-dimensional map and all other defects are not emphasized; and
  - a short defect mode in which only defects having a length below a predetermined shortness value are emphasized on said two-dimensional map and all other defects are not emphasized.

46. An apparatus for mapping a plurality of defects, according to claim 36, wherein said plurality of defects include a subset of angular defects out of axial alignment with the longitudinal central axis of said tubular member by a predetermined angular threshold, wherein said display means further includes:
- means for selectively displaying the presence of said defect as at least one indication on said two-dimensional map in one of a plurality of alternative modes, including an angular defect mode in which only said subset of angular defects out of axial alignment with said central longitudinal axis by said predetermined angular value are emphasized on said two-dimensional map and all other defects are not emphasized.

47. An apparatus for mapping a plurality of defects, according to claim 36, wherein said plurality of defects include a first subset of long defects having a length above a predetermined length value, a second subset of short defects having a length below a predetermined shortness value, and a third subset of angular defects out of axial alignment with the longitudinal central axis of said tubular member by a predetermined angular value, wherein said display means includes:
- means for selectively displaying the presence of said defect as at least one indication on said two-dimensional map in the following alternative modes:
  - a long defect mode in which only said first subset of long defects having a length above said predetermined length value are emphasized on said two-dimensional map and all other defect types are not emphasized;
  - a short defect mode in which only said second subset of short defects having a length below said predetermined shortness value are emphasized on said two-dimensional map and all other defect types are not emphasized; and an angle defect mode in which only said third subset of angular defects out of axial alignment with said longitudinal central axis by said predetermined angular value are emphasized on said two-dimensional map and all other defect types are not emphasized.

48. An apparatus for mapping a plurality of defects, according to claim 36, wherein said plurality of defects include a first subset of long defects having a length above a predetermined length value, a second subset of short defects having a length below a predetermined shortness value, and a third subset of angular defects out of axial alignment with the longitudinal central axis of said tubular member by a predetermined angular value, wherein said display means further includes:

means for selectively displaying the presence of said defect as one or more indications on said two-dimensional map in the following alternative modes:

a long defect mode in which only said first subset of long defects having a length above said predetermined length value are emphasized on said two-dimensional map and all other defect types are not emphasized;

a short defect mode in which only said second subset of short defects having a length below said predetermined shortness value are emphasized on said two-dimensional map and all other defect types are not emphasized;

an angle defect mode in which only said third subset of angular defects out of axial alignment with said longitudinal central axis by said predetermined angular value are emphasized on said two-dimensional map and all other defect types are not emphasized; and a full defect mode in which said first subset of long defects, said second subset of short defects, and said third subset of angular defects are simultaneously displayed on said two-dimensional map.

49. A method of mapping a plurality of defects, said plurality of defects being classified into a plurality of differing types of defects, including defects of differing shapes, lengths, and angular orientations, in a tubular member having a plurality of discrete solid segments, the sum of which comprise the entire solid volume of said tubular member, comprising the steps of:

generating at least one defect signal representing a defect in at least one discrete solid segment of said tubular member for each of said plurality of defects, each of said at least one defect signal having an amplitude value;

generating a longitudinal signal indicating the longitudinal position of said at least one discrete solid segment of said tubular member;

generating a circumferential signal indicating the circumferential position of said at least one discrete solid segment of said tubular member;

correlating said defect, longitudinal, and circumferential signals to obtain defect data, said defect data including the longitudinal position and circumferential position of said defect in said at least one discrete solid segment of said tubular member;

selectively displaying the presence of a selected one of said plurality of said differing types of defects as a plurality of indications in a two-dimensional map, said map including:

a first axis corresponding to the length of said tubular member;

a second axis corresponding to the circumference of said tubular member.

50. A method of mapping a plurality of defects, according to claim 49, wherein said plurality of defects include a plurality of defects of differing lengths, and said tubular member has a longitudinal central axis, and wherein said step of displaying comprises:

selectively displaying the presence of said defects in one of a plurality of alternative modes including a length of defect mode in which only a subset of defects of predetermined length value are emphasized on said two-dimensional map and all other defects are not emphasized.

51. A method of mapping a plurality of defects, according to claim 49, wherein said plurality of defects include a plurality of defects of differing lengths, and wherein said step of displaying comprises:

selectively displaying the presence of said defects in the following alternative modes:

a long defect mode in which only defects having a length above a predetermined length value are emphasized on said two-dimensional map and all other defects are not emphasized; and a short defect mode in which only defects having a length below a predetermined length value are emphasized on said two-dimensional map and all other defects are not emphasized.

52. A method of mapping a plurality of defects, according to claim 49, wherein said plurality of defects include a subset of angular defects out of axial alignment with the longitudinal central axis of said tubular member by a predetermined angular threshold, wherein the step of displaying comprises:

selectively displaying the presence of said defects in one of a plurality of alternative modes including an angular defect mode in which only said subset of angular defects out of axial alignment with said central longitudinal axis by said predetermined angular value are emphasized on said two-dimensional map and all other defects are not emphasized.

53. A method of mapping a plurality of defects, according to claim 49, wherein said plurality of defects include a first subset of long defects having a length above a predetermined length value, a second subset of short defects having a length below a predetermined shortness value, and a third subset of angular defects out of axial alignment with the longitudinal central axis of said tubular member by a predetermined angular value, wherein the step of displaying comprises:

selectively displaying the presence of said defects in the following alternative modes:

a long defect mode in which only said first subset of long defects having a length above said predetermined length value are emphasized on said two-dimensional map and all other defect types are not emphasized;

a short defect mode in which only said second subset of short defects having a length below said predetermined shortness value are emphasized on said two-dimensional map and all other defect types are not emphasized; and an angle defect mode in which only said third subset of angular defects out of axial alignment with said longitudinal central axis by said predetermined angular value are emphasized on said two-dimensional map and all other defect types are not emphasized.

54. A method of mapping a plurality of defects, according to claim 49, wherein said plurality of defects include a first subset of long defects having a length above a predetermined length value, a second subset of short defects having a length below a predetermined shortness value, and a third subset of angular defects out of axial alignment with the longitudinal central axis of said tubular member by a predetermined angular value, wherein the step of displaying comprises:
selectively displaying the presence of said defects in the following alternative modes:
a long defect mode in which only said first subset of long defects having a length above said predetermined length value are emphasized on said two-dimensional map and all other defect types are not emphasized;
a short defect mode in which only said second subset short defects having a length below said predetermined shortness value are emphasized on said two-dimensional map and all other defect types are not emphasized;
an angle defect mode in which only said third subset of angular defects out of axial alignment with said longitudinal central axis by said predetermined angular value are emphasized on said two-dimensional map and all other defect types are not emphasized; and
a full defect mode in which said first subset of long defects, said second subset of short defects, and said third subset of angular defects are simultaneously emphasized on said two-dimensional map.

55. A method of mapping a plurality of defects, according to claim 49, wherein said step of generating at least one defect signal comprises:
providing an inspection means including a plurality of flux detecting coils;
generating a magnetic flux in said tubular member;
detecting with said plurality of flux detecting coils said magnetic flux in said tubular member;
producing from said detected magnetic flux at least one signal representing a defect in at least one discrete solid segment of said tubular member for each of said plurality of defects, each of said at least one defect signal having an amplitude value; and
recording said amplitude value for each of said at least one defect signal.

56. A method of mapping a plurality of defects, according to claim 49, wherein said step of generating at least one defect signal comprises:
providing an inspection means including a plurality of flux detecting coils;
generating a magnetic flux in said tubular member;
detecting with said plurality of flux detecting coils said magnetic flux in said tubular member;
producing from said detected magnetic flux at least one signal representing a defect in at least one discrete solid segment of said tubular member for each of said plurality of defects, each of said at least one defect signal having an amplitude value;
recording said amplitude value for each of said at least one defect signal;
wherein said step of displaying comprises:
selecting at least one signal threshold;
comparing said at least one signal threshold to said amplitude value of each at least one defect signal to create a subset of datapoints ready for display; and
displaying said subset of datapoints to indicate the presence of said plurality of defects on said two-dimensional map.

* * * * *